US012773356B2

(12) United States Patent
Ingber et al.

(10) Patent No.: US 12,773,356 B2
(45) Date of Patent: Oct. 27, 2026

(54) VAGINAL FLUID ABSORPTION AND ODOR REDUCTION

(71) Applicant: LiviWell Inc., Pine Brook, NJ (US)

(72) Inventors: Michael Scott Ingber, Mendham, NJ (US); Dan Seewald, Pine Brook, NJ (US); Julie Marie Moore, Milford, CT (US)

(73) Assignee: LiviWell Inc., Pine Brook, NJ (US)

(*) Notice: Subject to any disclaimer, the term of this patent is extended or adjusted under 35 U.S.C. 154(b) by 0 days.

(21) Appl. No.: 19/320,454

(22) Filed: Sep. 5, 2025

(65) Prior Publication Data

US 2026/0000553 A1 Jan. 1, 2026

Related U.S. Application Data

(63) Continuation of application No. 19/058,199, filed on Feb. 20, 2025, now Pat. No. 12,447,064, which is a continuation of application No. 18/010,125, filed as application No. PCT/US2021/037329 on Jun. 15, 2021, now Pat. No. 12,496,234.

(Continued)

(51) Int. Cl.

| | |
|---|---|
| ***A61F 13/20*** | (2006.01) |
| ***A61F 6/06*** | (2006.01) |
| ***A61F 13/26*** | (2006.01) |
| ***A61L 15/20*** | (2006.01) |

(Continued)

(52) U.S. Cl.

CPC ............ *A61F 13/2065* (2013.01); *A61F 6/06* (2013.01); *A61F 13/2074* (2013.01); *A61F 13/266* (2013.01); *A61L 15/20* (2013.01); *A61L 15/26* (2013.01); *A61L 15/28* (2013.01)

(58) Field of Classification Search

CPC ........ A61F 5/44; A61F 5/453; A61F 13/2065; A61F 13/20; A61F 13/2074; A61F 13/26; A61F 13/266; A61F 13/34; A61F 2005/4402; A61F 6/06; A61F 6/18;

(Continued)

(56) References Cited

U.S. PATENT DOCUMENTS 2,733,714 A * 2/1956 Hass .................. A61F 13/2051 604/14
3,431,909 A * 3/1969 Krusko .................. A61F 13/20

(Continued)

FOREIGN PATENT DOCUMENTS

WO WO-0006072 A2 * 2/2000 ......... A61F 13/2051

*Primary Examiner* — Alireza Nia
*Assistant Examiner* — Michael Milo
(74) *Attorney, Agent, or Firm* — Erise IP, P.A.

(57) ABSTRACT

A device includes a shell including a proximal end and a distal end of the shell. The device also includes a plunger within the shell. The plunger can include a flexible stop at a proximal end of the plunger and a distal end. The device can further include an absorptive unit configured to absorb fluid within a vaginal cavity. The absorptive unit can be affixed to the distal end of the plunger. The absorptive unit can include an absorptive element affixed to a frame structure configurable to reversibly transition between a compressed and uncompressed configuration. The absorptive unit can also include a tether coupled to the absorptive unit via the frame structure. The tether can extend through the proximal end of the plunger. Related methods of use are also described.

20 Claims, 21 Drawing Sheets

Related U.S. Application Data

(60) Provisional application No. 63/039,654, filed on Jun. 16, 2020.

(51) Int. Cl.
*A61L 15/26* (2006.01)
*A61L 15/28* (2006.01)

(58) Field of Classification Search
CPC .......... A61F 6/144; A61F 6/245; A61L 15/20; A61L 15/26; A61L 15/28; A61M 31/00
USPC .......................................................... 128/832
See application file for complete search history.

(56) References Cited

U.S. PATENT DOCUMENTS

| | | | | | |
|---|---|---|---|---|---|
| 3,683,915 | A * | 8/1972 | Voss | A61F 13/2051 | |
| 3,762,413 | A * | 10/1973 | Hanke | A61F 13/2051 | 604/385.18 |
| RE33,839 | E * | 3/1992 | Chmelir | A61L 15/60 | 977/841 |
| 6,645,136 | B1 * | 11/2003 | Zunker | A61F 2/005 | 128/885 |
| 2002/0177835 | A1 * | 11/2002 | Zadini | A61B 17/12099 | 604/385.18 |
| 2005/0277904 | A1 * | 12/2005 | Chase | A61F 13/2065 | 604/385.18 |
| 2015/0065942 | A1 * | 3/2015 | De Soto-Burt | A61F 13/26 | 604/15 |
| 2016/0235583 | A1 * | 8/2016 | Durling | A61F 6/12 | |

* cited by examiner

VAGINAL FLUID ABSORPTION AND ODOR REDUCTION

CROSS-REFERENCE TO RELATED APPLICATIONS

This patent application is a continuation application claiming priority benefit, with regard to all common subject matter, of U.S. patent application Ser. No. 19/058,199, filed Feb. 20, 2025, and entitled "VAGINAL FLUID ABSORPTION AND ODOR REDUCTION" ("the '199 application"). The '199 application is a continuation application claiming priority benefit, with regard to all common subject matter, of U.S. Patent Application Ser. No. 18/010,125, filed Dec. 13, 2022, and entitled "VAGINAL FLUID ABSORPTION AND ODOR REDUCTION" ("the '125 application"). The '125 application is a national stage application, filed under 35 § U.S.C. 371, of International Patent Application PCT/US2021/037329 filed on Jun. 15, 2021, which claims priority under 35 U.S.C. § 119 (e) to U.S. Provisional Patent Application No. 63/039,654 filed Jun. 16, 2020. The above-referenced applications are hereby incorporated by reference in their entirety into the present application.

BACKGROUND

Absorption of semen from within the vaginal cavity can be important for maintaining vaginal health and hygiene. Feminine hygiene products can be used to absorb fluids emanating from or located within a vaginal cavity of a female. Following intercourse, it can be desirable to remove fluids, such as semen, from the vaginal cavity to maintain vaginal hygiene, reduce vaginal discomfort, and to reduce vaginal odor. Vaginal odor can develop due to semen persisting within the vaginal cavity following coitus. Semen can reduce the acidity within the vaginal cavity, and the subsequent change in pH balance and fluid itself can exacerbate vaginal odor and can cause urinary tract infections and vaginitis. Conventional feminine hygiene products, such as tampons, pads, and/or cups, may be configured to absorb menstrual fluids, but may not adequately absorb seminal fluid due to the shape of the products, the type of materials used in the products, and method for using conventional feminine hygiene products. Accordingly, there remains a need for devices and methods for absorbing semen and reducing vaginal odor and discomfort within the vaginal cavity.

Semen can be removed from the vaginal cavity following intercourse by self-evacuation or by manual or digital insertion of material into the vaginal cavity. The materials can include paper products and feminine hygiene products. Such materials are not sufficiently absorbent to adequately remove a sufficient amount of semen from the vaginal cavity, which can increase the likelihood of vaginal odor and/or more complicated vaginal health conditions such bacterial vaginosis or other vaginal infections. In addition, these methods of semen removal do not provide absorption in more remote regions of the vaginal cavity, such as the vaginal apex and fornices. Instead, these methods and materials often rely on gravity or self-evacuation to absorb semen only from portions of the vaginal cavity in proximity to the vaginal opening. As a result, semen can persist within the vaginal cavity and may not be adequately removed or absorbed.

SUMMARY

In an aspect, a device includes a shell including a proximal end and a distal end. The device can include a plunger within the shell. The plunger can include a flexible stop at a proximal end of the plunger and a distal end. The device can also include an absorptive unit configured to absorb fluid within a vaginal cavity. The absorptive unit can be affixed to the distal end of the plunger. The absorptive unit can include an absorptive element affixed to a frame structure. The absorptive unit can further include a tether coupled to the absorptive unit via the frame structure. The tether can extend through the proximal end of the plunger.

One or more of the following features can be included in any feasible combination. For example, the frame structure can include a plurality of frame structure extensions and the absorptive unit can include a plurality of absorptive elements, such that each frame structure extension is positioned within a corresponding absorptive element. The tether can be coupled to the absorptive unit via the frame structure extension. The frame structure can also include an injection molded frame structure configurable to transition between a compressed configuration and an uncompressed configuration and to transition between the uncompressed configuration and the compressed configuration. The tether can be coupled to the absorptive unit via the frame structure extension. The absorptive element or at least one absorptive element of the plurality of absorptive elements can include at least one of a contraceptive, a spermicide, and a medication for disease prevention or treatment. The absorptive element or at least one absorptive element of the plurality of absorptive elements can absorb fluid at an effective rate. The absorptive element or at least one absorptive element of the plurality of absorptive elements can be configured to expand within the vaginal cavity and to conform to anatomical features within the vaginal cavity.

The plurality of absorptive elements can be configured in a longitudinally overlapping manner within the shell. The plurality of absorptive elements can be configured in a circumferentially overlapping manner within the shell. The absorptive element or at least one absorptive element of the plurality of absorptive elements can be configured to absorb seminal fluid. The device can be configured to partially deploy the absorptive unit within the vaginal cavity in response to advancing the plunger within the shell to cause the flexible stop to engage the proximal end of the shell. The device can be further configured to fully deploy the absorptive unit within the vaginal cavity in response to advancing the plunger within the shell to cause the flexible stop to advance past the proximal end of the shell. The device can be configured to retract the absorptive unit into the shell by retracting the plunger within the shell. The device can include a flexible head positioned at the distal end of the shell. The shell can be formed from one of a thermoplastic resin, recycled paper, plant-based bioplastics, biodegradable polymers, or a combination thereof.

The flexible stop, and the flexible head can be formed from a thermoplastic elastomer having a durometer between 25 and 65 as measured on the Shore A durometer scale. The absorptive element or at least one absorptive element of the plurality of absorptive elements can be an expandable polyurethane sponge. The proximal end of the shell can include a gripping area including one or more protrusions configured to aid a user in grasping the device. The absorptive element or at least one absorptive element of the plurality of absorptive elements can include hyaluronic acid and/or boric acid. The absorptive element or at least one absorptive element of the plurality of absorptive elements can be configured to reduce odor within the vaginal cavity.

In another aspect, a method includes inserting a fluid absorption device into a vaginal cavity. The fluid absorption device can include a shell, a plunger within the shell, and an absorptive unit affixed to a distal end of the plunger. The absorptive unit can include an absorptive element affixed to a frame structure, and a tether coupled to the absorptive unit via the frame structure. The method can also include advancing the plunger within the shell to cause the absorptive unit to deploy within the vaginal cavity and to conform to a shape of the vaginal cavity. The method can further include absorbing, by the absorptive element, fluid present within the vaginal cavity. The method can also include removing the shell and the plunger from the vaginal cavity.

One or more of the following features can be included in any feasible combination. For example, the method can include advancing the plunger within the shell can include advancing the plunger to a first position at which a flexible stop of the plunger engages a proximal end of the shell and deploying the absorptive unit partially within the vaginal cavity. The method can also include advancing the plunger within the shell can further include advancing the plunger to a second position at which the flexible stop is advanced past the proximal end of the shell causing the frame structure to transition from a compressed configuration to an uncompressed configuration and deploying the absorptive unit fully within the vaginal cavity. The method can also include retracting the absorptive unit into the shell by retracting the plunger within the shell causing the frame structure to transition from the uncompressed configuration to the compressed configuration within the shell.

The frame structure can include a plurality of frame structure extensions and the absorptive unit includes a plurality of absorptive elements, such that each frame structure is within the absorptive element. The frame structure can include an injection molded frame structure configurable to transition between a compressed configuration and an uncompressed configuration and to transition between an uncompressed configuration and a compressed configuration. The tether can be coupled to the absorptive unit via the frame structure extension. The absorptive element or at least one absorptive element of the plurality of absorptive elements can include at least one of a contraceptive, a spermicide, and a medication for disease prevention or treatment. The absorptive element or at least one absorptive element of the plurality of absorptive elements can absorb fluid at a rate of 1-2 ml/min, 2-3 ml/min, 3-4 ml/min, 4-5 ml/min, 5-6 ml/min, 6-7 ml/min, 7-8 ml/min, 8-9 ml/min, 9-10 ml/min, or 10-15 ml/min. The absorptive element or at least one absorptive element of the plurality of absorptive elements can be configured to expand within the vaginal cavity and to conform to anatomical features within the vaginal cavity.

The plurality of absorptive elements can be configured in a longitudinally overlapping manner within the shell. The plurality of absorptive elements can be configured in a circumferentially overlapping manner within the shell. The absorptive element or at least one absorptive element of the plurality of absorptive elements can be configured to absorb seminal fluid. The device can include a flexible head positioned at the distal end of the shell. The shell can be formed from one of a thermoplastic resin, recycled paper, plant-based bioplastics, biodegradable polymers, or a combination thereof.

The flexible stop, and the flexible head can be formed from a thermoplastic elastomer having a durometer between 25 and 65 as measured on a Shore A durometer scale. The absorptive element or at least one absorptive element of the plurality of absorptive elements can be an expandable polyurethane sponge. The proximal end of the shell can include a gripping area including one or more protrusions configured to aid a user in grasping the fluid absorption device. The method can also include removing the absorptive unit from within the vaginal cavity by pulling the tether, the plunger, the shell, and any combination thereof. The absorptive element or at least one absorptive element of the plurality of absorptive elements can include hyaluronic acid and/or boric acid. The absorptive element or at least one absorptive element of the plurality of absorptive elements can be configured to reduce odor within the vaginal cavity.

DESCRIPTION OF DRAWINGS

These and other features will be more readily understood from the following detailed description taken in conjunction with the accompanying drawings, in which.

It is noted that the drawings are not necessarily to scale. The drawings are intended to depict only typical aspects of the subject matter disclosed herein, and therefore should not be considered as limiting the scope of the disclosure.

DETAILED DESCRIPTION

The subject matter described herein provides a device and method of use for absorbing semen from the vaginal cavity and preventing vaginal odor reduction. The device and methods of use described herein can absorb semen and reduce vaginal odor. For example, the device includes absorptive elements that can be configured to absorb semen at a greater rate compared to the materials of traditional feminine hygiene products, which are configured specifically for menstrual fluid absorption as opposed to semen absorption. The absorptive unit also includes materials and features enabling expansion of the absorptive elements within the vaginal cavity. Additionally, the absorptive elements can be specially shaped to enhance expansion and provide increased absorbency of semen. In this way, the device described herein can interface with a large percentage of the vaginal cavity where semen may be present and can absorb semen from apical locations within the vaginal cavity.

The device also includes features enabling a user to perform semen absorption in multiple deployment configurations of the device, depending on the intended or desired method of use. For example, a user may remove semen quickly from introital regions of the vaginal cavity, such as the vaginal opening, using the device in a partial deployment configuration suited for shortened periods of manual use. The user can also remove semen over a more prolonged period of use, such as hours, or overnight, using the device in a full deployment configuration. The device described herein therefore address the needs for semen absorption and vaginal odor reduction within the vaginal cavity.

Figure 1:
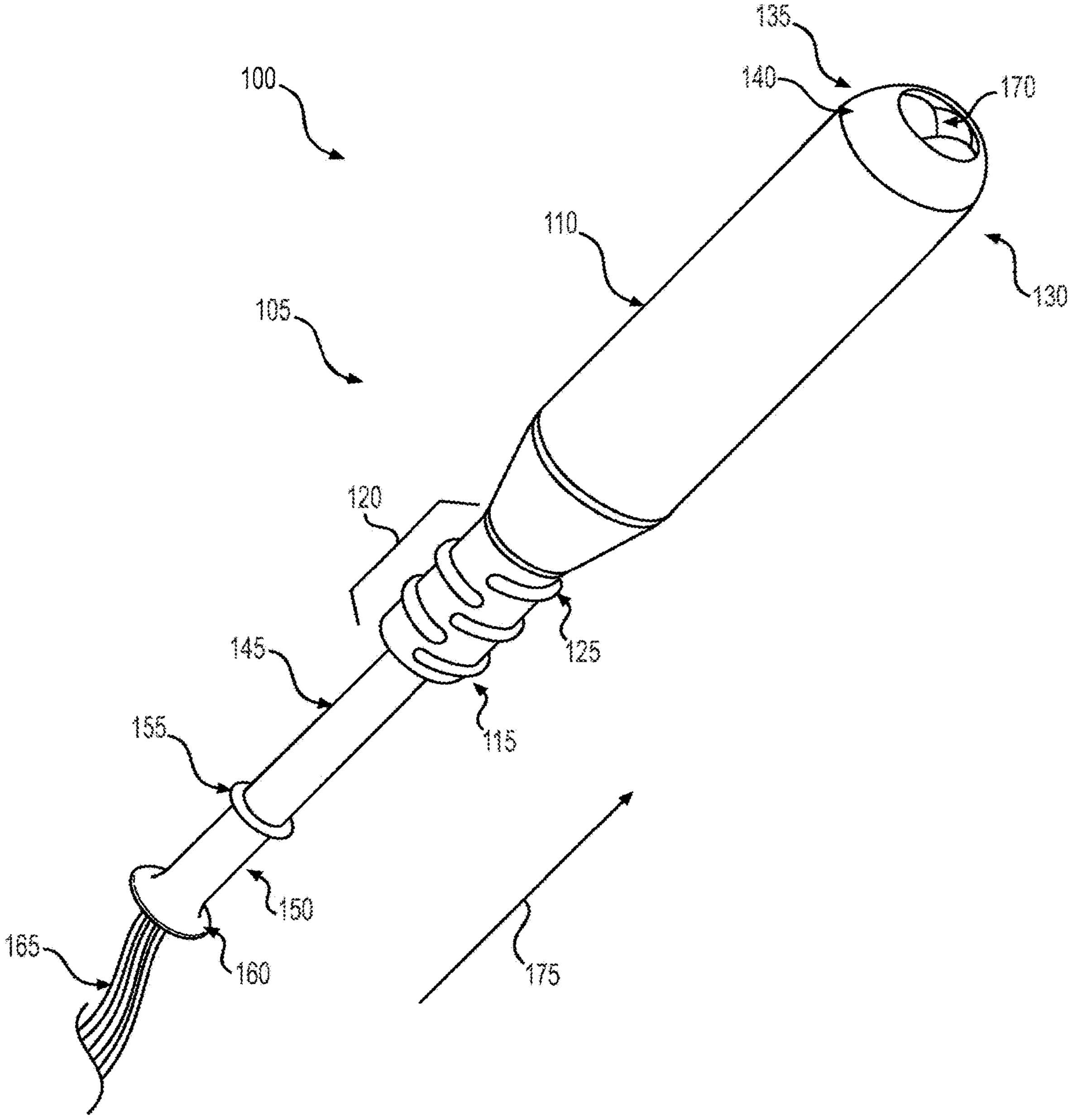
FIG. 1 is a diagram illustrating an exemplary embodiment of a device for vaginal fluid absorption and odor reduction according to some implementations of the current subject matter.

FIG. 1 is a diagram 100 illustrating an exemplary embodiment of a device 105 for vaginal fluid absorption and odor reduction according to some implementations of the current subject matter. As shown in FIG. 1, the device 105 includes a shell 110, a plunger 145 within the shell, and an absorptive unit 170. The device 105 can be inserted along an insertion axis 175 into the vaginal cavity to absorb fluid within the vaginal cavity. The plunger 145 can be advanced within the shell 110 to cause the absorptive unit 170 to deploy from the shell 110 within the vaginal cavity. Fluids within the vaginal cavity can be absorbed by the absorptive unit 170. The device 105 is intended for use as a single-use, disposable, sanitary device. The device 105 can be used without requiring sterilization before use.

The shell 110 includes a proximal end 115 and a distal end 130. In some embodiments, the shell 110 can be formed from and can include a thermoplastic resin, recycled paper, plant-based bioplastics, biodegradable polymers, or a combination thereof. In embodiments described herein, the shell 110 can be formed from a thermoplastic elastomer or a thermoplastic polyurethane having a durometer between 85 and 95, as measured on the Shore A durometer scale. In embodiments described herein, the device 105 can include a non-plant-based bioplastic. The proximal end 115 can include a gripping area 120 configured to aid a user in grasping or otherwise securing the device 105 for manual insertion into or removal from the vaginal cavity. The gripping area 120 can include one or more protrusions 125. In some embodiments, the protrusions 125 can be bumps or raised circular protrusions. In some embodiments, the protrusions 125 can be raised protrusions extending around a portion of the circumference of the proximal end 115 of the shell 110. A variety of protrusion 125 shapes can be included without limitation.

As shown in FIG. 1, the distal end 130 of the shell 110 includes a flexible head 135. The flexible head 135 can include at least one flexible head member 140. The flexible head 135 and the flexible head member 140 can be configured as atraumatic components, which can reduce the likely hood of tissue damage or trauma when inserting the device 105 into the vaginal cavity or when deploying the absorptive unit 170 within the vaginal cavity. In some embodiments, the flexible head 135 and/or the flexible head member 140 can be formed from a thermoplastic elastomer or a thermoplastic polyurethane having a durometer between 25 and 65, as measured on the Shore A durometer scale. In some embodiments, the flexible head 135 and/or the flexible head member 140 can be formed from the same material used to form the shell 110. In some embodiments, the flexible head 135 and flexible head member 140 can include an annular shape, or a frustoconical shape. In some embodiments, the flexible head 135 can include a plurality of flexible head members 140 shaped as concentric rings.

Other atraumatic shapes and configurations of the flexible head 135 and the flexible head members 140 can be included without limitation. For example, the flexible head 135 and the flexible head members 140 can be configured so as to avoid restricting deployment and/or retraction of the absorptive unit 170 and any absorptive elements included in the absorptive unit. In some embodiments, the flexible head 135 and/or the flexible head members 140 can be configured with a petal-shaped configuration. In some embodiments, the flexible head 135 can be open and may not include a flexible head member 140. The flexible head 135 and/or the flexible head members 140 can be configured so as to avoid damage to the vaginal mucosa during insertion into the vaginal cavity. In addition, the flexible head 135 and/or the flexible head members 140 can be configured so as to reduce or limit expulsion of absorbed vaginal fluids and/or semen from within the absorptive unit 170 as the absorptive unit 170 is retracted into the shell 110.

In some embodiments, the flexible head 135 and/or the flexible head members 140 can be configured to control the deployment of the absorptive unit 170 from within the shell 110. The flexible head 135 and/or the flexible head members 140 can be configured with a geometry or material type to provide a force of friction against the absorptive unit 170 during deployment and thus provide a user with greater control when advancing the plunger 145 to deploy the absorptive unit 170 within the vaginal cavity. In some embodiments, the device 105 may not include a flexible head 135.

As shown in FIG. 1, the device 105 includes a plunger 145. The plunger 145 can be configured within the shell 110 and can include a proximal end 150, a flexible stop 155, a plunger flange 160, and a distal end. The plunger 145 can be positioned within the shell 110 and can be movable to cause the absorptive unit 170 to deploy from or retract into the shell 110. The plunger 145 can include an inner volume therein and can contain the tether 165. The hollow plunger 145 can move axially with respect to the tether 165 contained therein.

The plunger 145 includes a flexible stop 155 at the distal end 150. The flexible stop 155 can be configured as a deployment indicator for both deployment and recapture of the absorbent unit 170. The flexible stop 155 can be formed from a thermoplastic elastomer having a durometer between 25 and 65, as measured on the Shore A durometer scale. In some embodiments, the flexible stop 155 can be formed from the same material used to form the shell 110. The flexible stop 155 can enable a user to ascertain an amount of deployment of the absorptive unit 170 within the vaginal cavity based on the position of the flexible stop 155 with respect to an opening at the proximal end 115 of the shell 110. For example, after insertion of the device 105 into the vaginal cavity, a user can advance the plunger 145 so that the flexible stop 155 abuts or engages the opening of proximal end 115 of the shell 110 to cause the absorptive unit to partially deploy into the vaginal cavity from within the shell 110. A user can advance the plunger 145 further so that the flexible stop 155 progresses beyond the opening at the proximal end 115 of the shell 110, such that the flexible stop 155 is positioned within the proximal end 115 of the shell 110 and that the plunger flange 160 abuts or engages the proximal end 115 of the shell 110. The plunger flange 160 can further enable a user to discern the degree to which the absorptive unit is deployed from within the shell 110.

As shown in FIG. 1, the device 105 includes a tether 165. The tether 165 can be formed from one or more strings and can be coupled to the absorptive unit 170. In some embodiments, the tether 165 can coupled to the absorptive unit 170 via a frame structure configured within the absorptive unit 170. The tether 165 is configured within the plunger 145. The tether 165 can extend through the plunger 145 and can exit via the plunger flange 160. The tether 165 can enable a user to remove the absorptive unit 170 from within the vaginal cavity by pulling the tether 165. The tether 165 can be formed from cotton, rayon, nylon, polyester, polyethylene, or a blend thereof. In some embodiments, the tether 165 can include non-toxic, organic materials. In some embodiments, the tether 165 can be a non-sterile suture material. The tether 165 can include a single strand that can be knotted or twisted.

As further shown in FIG. 1, the device 105 includes an absorptive unit 170. The absorptive unit 170 can be retained in a compressed state within the shell 110 during shipping, prior to use of the device, as well as when retracted into the shell 110. The absorptive unit 170 is shown in an undeployed configuration as may be provided by the manufacturer prior to use. The absorptive unit 170 can be coupled to the tether 165 and can be configured within the distal end 130 of the shell 110. In some embodiments, the absorptive unit 170 can include one or more absorptive elements. The absorptive unit 170 and the absorptive elements can include expandable polyurethane sponge material configured to expand within the vaginal cavity and provide greater absorption of vaginal fluids, such as semen. In some embodiments, the absorptive unit 170 and the absorptive elements can include a polyester material. In some embodiments, the absorptive unit 170 can include non-toxic, organic materials. Additional details of the absorptive unit 170 and the absorptive elements will be shown and described in relation to FIGS. 2-5.

Figure 2:
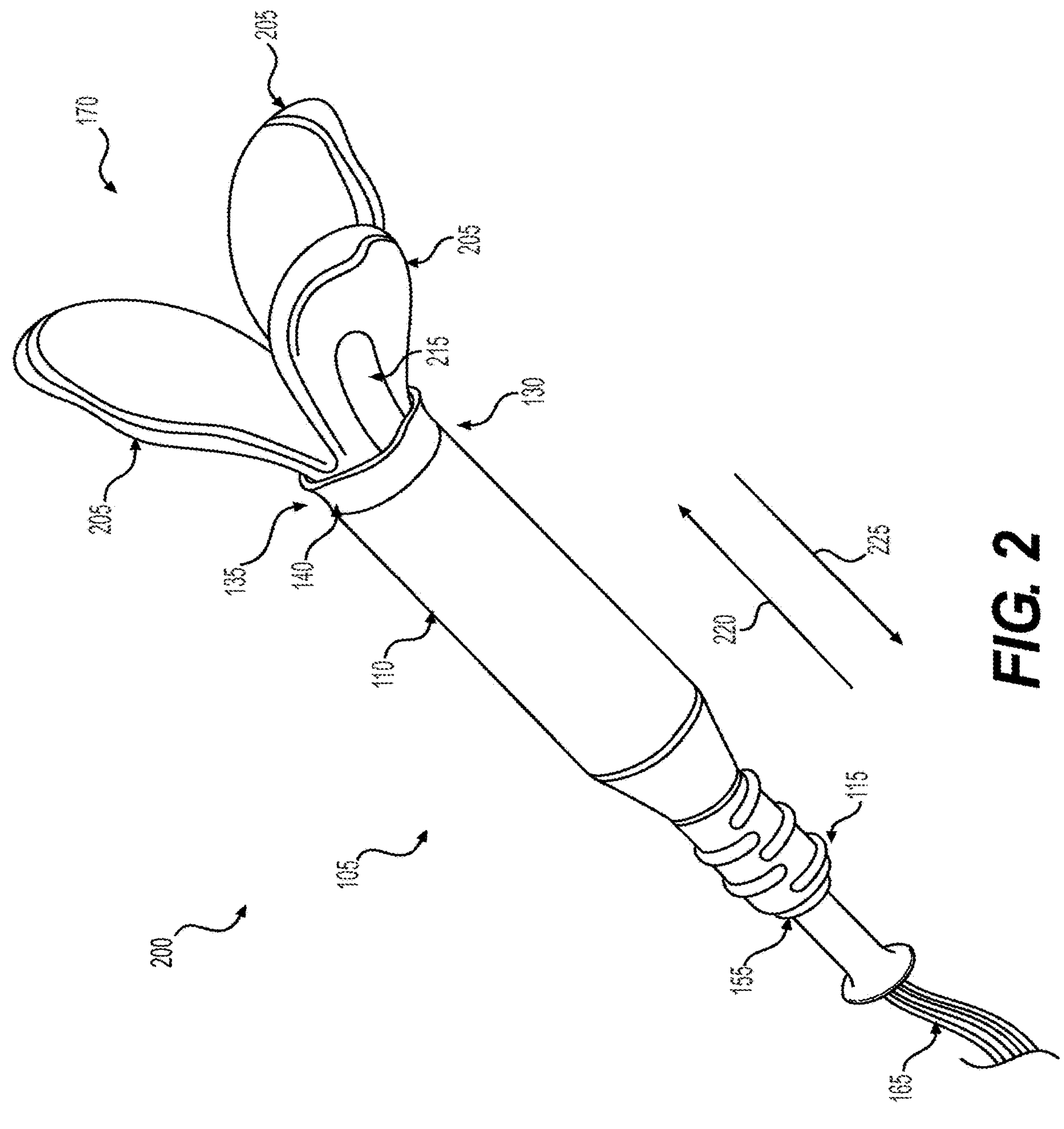
FIG. 2 is a diagram illustrating an exemplary embodiment of the device of FIG. 1 in a partially deployed configuration according to some implementations of the current subject matter.

FIG. 2 is a diagram 200 illustrating an exemplary embodiment of the device 105 of FIG. 1 in a partially deployed configuration according to some implementations of the current subject matter. As shown in FIG. 2, the plunger 145 has been advanced along the deployment axis 220 such that the flexible stop 155 is engaged with the opening at the proximal end 115 of the shell 110 to cause the absorptive unit 170 to partially deploy from the flexible head 135. In this partial deployment configuration, a user can digitally or manually maneuver the device 105 within the vaginal cavity to place the absorptive unit 170 in contact with the fluids to be absorbed. A user can retract the absorptive unit 170 into the shell by pulling the plunger 145 along the retraction axis 225 causing the absorptive unit 170 to be retained within the shell 110.

The absorptive unit 170 can include one or more absorptive elements 205. For example, in the embodiment shown in FIG. 2, the absorptive unit 170 includes three absorptive elements 205. The absorptive unit 170 can include one, two, three, four, five, six, seven, eight, nine, or ten absorptive elements 205. The absorptive elements 205 can include a high-density polyester polyurethane that has a fine (or small) pore structure and fully open cells. The high-density polyester polyurethane can include a large surface area configured for enhanced absorption. In embodiments described herein, the absorptive elements 205 can be a dry or pre-moistened sponge, such as a polyurethane sponge configured to absorb seminal fluids. In some embodiments, the absorptive elements 205 can include a contraceptive, a spermicide, and/or a medication for disease treatment or prevention, such as a medication used in the treatment sexually transmitted diseases. The absorptive elements 205 can include hyaluronic acid and/or boric acid. The presence of semen within the vaginal cavity can cause discomfort therein and can cause the normally acidic conditions of the vaginal cavity to become more basic, which can result in vaginal odor. By including hyaluronic acid and/or boric acid in the absorptive elements 205 odor reduction can be facilitated by altering the chemistry within the vaginal cavity from a basic environment to a more acidic environment. In some embodiments, a portion of the absorptive elements 205 can include a color-changing agent causing the portion of the absorptive element to change color in response to contacting semen. In this way, the device 105 can provide a user with visual feedback to confirm that the absorptive elements 205 have contacted and absorbed semen from within the vaginal cavity.

The material of the absorptive elements 205 can have one or more physical properties associated with each of the three material configurations shown in Table 1.

TABLE 1

| Configuration | 1 | 2 | 3 |
|---|---|---|---|
| Density (kg/m$^3$) | 32.0 | 80.0 | 96.1 |
| Tensile strength (kPa) | 227.5 | 227.5 | 172.3 |
| Elongation % | 435 | 394 | 500 |
| Tear strength (kPa) | 23.44 | 23.44 | 24.13 |
| CLD (kPa) | | | |
| @ 10% R | | | 4.83 |
| @ 25% R | 3.10 | 6.21 | 5.86 |
| @ 65% R | 4.83 | 13.10 | 15.86 |
| Compression Set (%) | 8 | 6 | 2.3 |
| Pore Size (ppmm) | 4.33 | 4.33 | 4.33 |
| Reticulation Method | Thermal | Thermal | Thermal |

As presented in Table 1, "Elongation" can correspond to a measure indicating an extent to which a material can be stretched before it breaks and is expressed as a percentage of its original size or length.

As presented in Table 1, "Tear Strength" can correspond to a measure of a measure of the force required to continue a tear in foam after a split has been started.

As presented in Table 1, "CLD" can correspond to a compression load deflection measurement and can indicate a measure of firmness or a minimum load to deflect a 1" (2.54 cm) sample by a percentage of its original thickness. As such, CLD or compression force deflection (CFD) testing can be performed at various % R values to measure the minimum amount of load or force to cause deflection of a 1" (2.54 cm) test sample. For example, as shown in Table 1, the absorptive elements 205 of configuration 3 require a minimum force of 4.83 kPa to compress the absorptive element 205 to 2.286 cm (corresponding to a 10% deflection of the 2.54 cm test piece).

As presented in Table 1, "Compression Set" can correspond to a measure of the permanent deformation of a foam after it has been compressed between two metal plates for a controlled time period and temperature condition. The standard conditions are 22 hours at 70° C. (158° F.). The foam is compressed to a thickness given as a percentage of its original thickness, usually 50%. Compression set is expressed as the percentage of its original thickness that remained "set". For example: If a 2"×2"×1" sample measured 1.00 inch (2.54 cm) before compression and 0.95 inch after the test, it is reported to have a compression set value of 5%, i.e., it did not recover 5% of its original thickness.

As presented in Table 1, "Reticulation Method" can correspond to a post-processing technique in foam manufacturing that can remove window membranes from cells of the foam.

In some embodiments, the absorptive elements 205 can include a sponge material, such as a polyurethane sponge which can absorb semen at an effective rate of 1-2 ml/min, 2-3 ml/min, 3-4 ml/min, 4-5 ml/min, 5-6 ml/min, 6-7 ml/min, 7-8 ml/min, 8-9 ml/min, 9-10 ml/min, or 10-15 ml/min. In some embodiments, the absorption of vaginal fluids and/or semen by the absorptive unit 170 and/or absorptive elements 205 can be increased by manual manipulation of the device 105 within the vaginal cavity. In this way, the absorptive unit 170 and/or absorptive elements 205 can be placed in contact with the vaginal mucosa to absorb a greater amount of vaginal fluids and/or semen or to absorb fluids at a greater rate than passive absorption, which can occur in response to a user deploying the absorptive unit 170 within the vaginal cavity for longer periods of time.

As shown in FIG. 2, one or more absorptive elements 205 may include a portion of a frame structure positioned within one or more of the absorptive elements 205. For example, as shown in FIG. 2, a frame structure extension 215 can be positioned within the absorptive element 205. The frame structure extension 215 can be included in a frame structure 210 as shown in FIG. 3.

Figure 3:
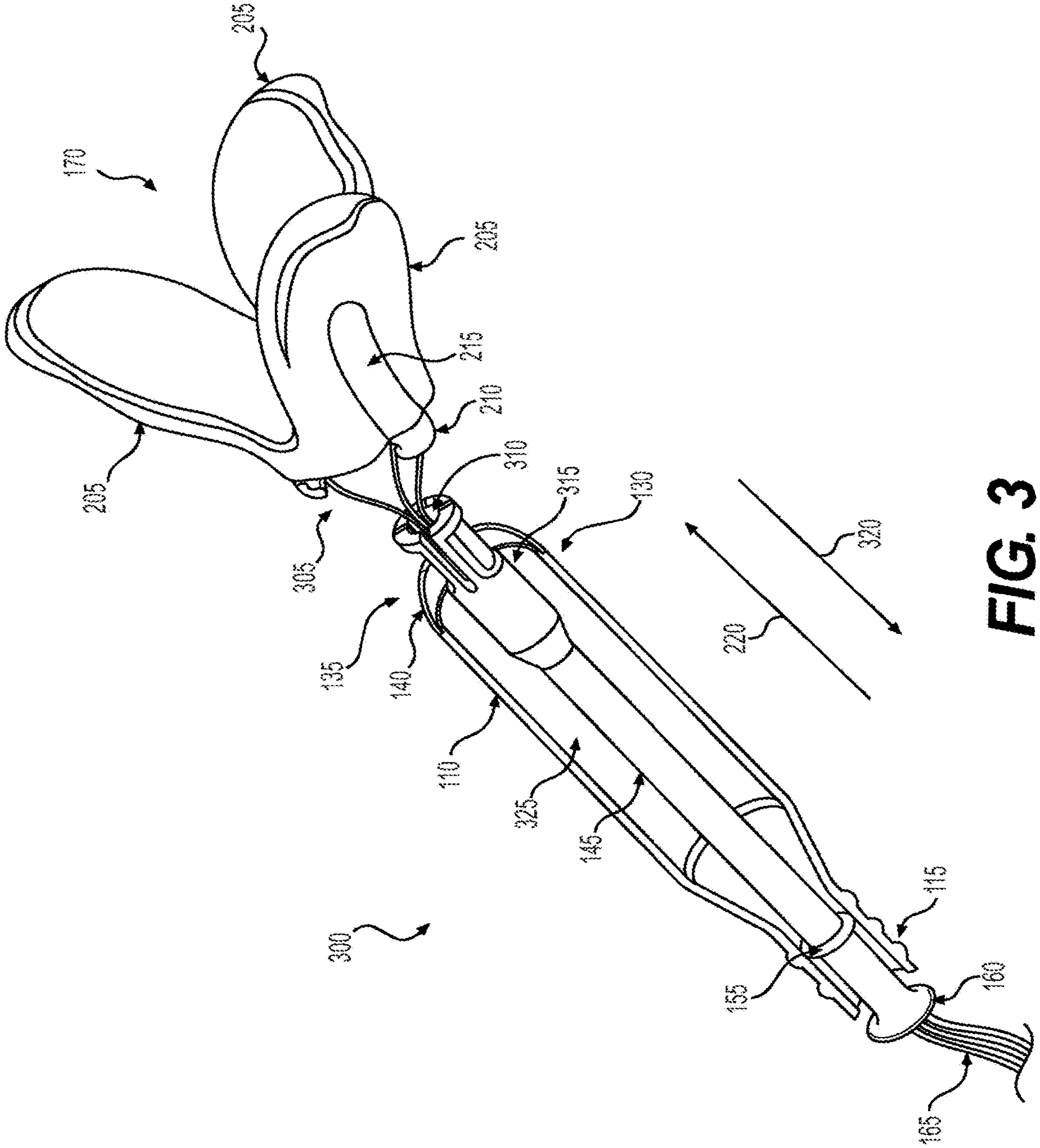
FIG. 3 is a diagram illustrating an exemplary embodiment of the device of FIG. 1 in a fully deployed configuration according to some implementations of the current subject matter.

FIG. 3 is a diagram 300 illustrating an exemplary embodiment of the device 105 of FIG. 1 in a fully deployed configuration according to some implementations of the current subject matter. As shown in FIG. 3, the plunger 145 has been advanced along the deployment axis 220 such that the flexible stop 155 has travelled beyond the opening at the proximal end 115 of the shell 110 and is positioned within the proximal end 115 of the shell 110. In this fully deployed configuration, the plunger flange 160 is abutting or engaged with the proximal end 115 of the shell 110 and the absorptive unit 170 has been fully deployed from the flexible head 135 within the vaginal cavity to absorb any fluids contacting the absorptive unit. A user can remove shell 110 and the plunger 145 by grasping the device 105 via the plunger 145, the shell 110, or a combination there and pulling along the removal axis 320 to withdraw the shell 110 and the plunger 145 from within the vaginal cavity leaving the absorptive unit 170 to be retained within the vaginal cavity for fluid absorption. A user can remove the absorptive unit 170 from the vaginal cavity by pulling the tether 165.

At least one of the absorptive elements may include a frame structure 210. The frame structure 210 can be formed via injection molding or compression molding methods. The frame structure 210 can include a plastic frame structure, a metal wire frame structure, or a laminated frame structure including a metal material and a plastic material. The frame structure 210 can also include a laminated frame structure 210 formed from plastics of two differing durometers. The frame structure 210 can include one or more frame structure extensions 215 to which the tether 165 can be affixed. The frame structure 210 can facilitate expansion of the absorptive elements 205 within the vaginal cavity. The frame structure 210 can assist expanding the absorptive elements 205 from the un-deployed configuration shown in FIG. 1. As a result, the frame structure 210 can enable the absorptive elements 205 to more readily conform to the anatomical features within the vaginal cavity, which can increase the rate of fluid absorption from a larger percentage of the volume of the vaginal cavity. The absorptive element can include a coupling portion 305 at which the tether 165 can be coupled to the frame structure 210. In some embodiments, the absorptive element 205 can be coupled directly to the tether 165 and may not include a frame structure 210. As shown in FIG. 3, the tether 165 includes three strings, each string coupled to one of the three absorptive elements 205. In some embodiments, the tether 165 can include more strings or less strings than the number of absorptive elements 205 included in the absorptive unit 170. For example, in some embodiments, the absorptive unit 170 can include a single absorptive element 205 and a plurality of strings of the tether 165 can be coupled to the single absorptive element 205. In other embodiments, the absorptive unit 170 can include a plurality of absorptive elements 205 coupled to a single string or a single tether 165.

The plunger 145 may be formed as a hollow structure positioned with the shell lumen 325. The plunger 145 can include an opening 310 at the distal end 315 of the plunger 145. The opening 310 can allow the tether 165 to travel axially within the plunger 145 and to exit the distal end 315 of the plunger 145 to couple with the absorptive elements 205 via the frame structure 210. In this way the plunger 145 (and shell 110) can be removed from the vaginal cavity, leaving the absorptive unit 170 within the vaginal cavity and the tether 165 extending out from the vaginal cavity.

As shown in FIG. 3, the absorptive unit 170 may include three absorptive elements 205. The absorptive elements 205 can be formed in a variety of shapes including, but not limited to, petal, trumpet, campanulate, saucer, funnelform, urceolate, bowl, and papilionaceous or butterfly shapes. In some embodiments, one or more of the absorptive elements 205 can be conical shaped. In some embodiments, the absorptive elements 205 can be configured in a longitudinally overlapping manner within the shell 110. This configuration can be partially seen in FIG. 1, when viewing the three absorptive elements comprising the absorptive unit 170 through the flexible head 135 at the distal end 130 of the shell 110. In some embodiments, the absorptive elements can be configured in a circumferentially overlapping manner with the shell 110. For example, the absorptive elements 205 can be arranged to overlap with one another with respect to a circumference of the shell 110.

Figure 4:
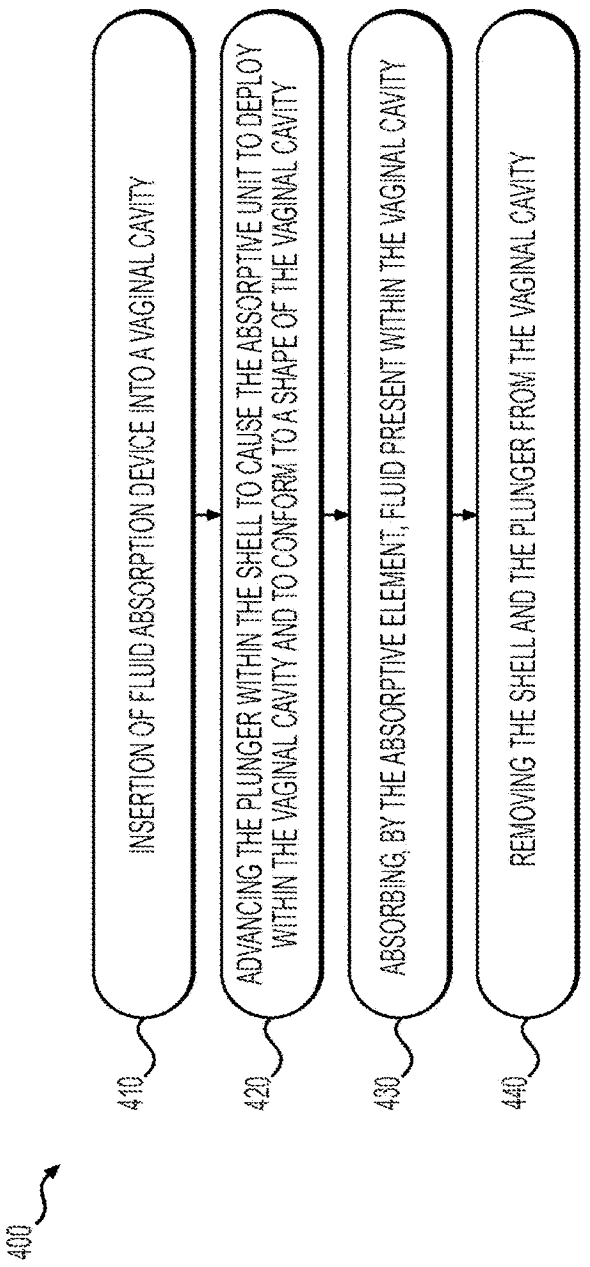
FIG. 4 is a process diagram illustrating a method for using the device of FIGS. 1-3 for vaginal fluid absorption and odor reduction according to some implementations of the current subject matter.

FIG. 4 is a process diagram 400 illustrating a method for using a device of the present invention such as device 105 of FIG. 1 for vaginal fluid absorption and odor reduction according to some implementations of the current subject matter. The method 400 can be performed to absorb or remove semen from within the vaginal cavity. For example, a user may perform the method following vaginal intercourse. The user may perform the method using the device 105 to maintain vaginal hygiene and to reduce vaginal odor. The description of the method of FIG. 4 will be provided in relation to the description of the device 105 and embodiments shown in FIGS. 1-3.

At 410, a fluid absorption device 105 can be inserted into a vaginal cavity of a user. A user may remove the device 105 from a protective packaging provided by the manufacturer of the device prior to insertion. In some embodiments, the protective packaging can include a label. The label can include instructions informing a user that the device 105 is a single-use device and is intended to be disposed of after the single-use. The label can also include instructions informing the user about the use of the device 105. The device 105 and its packaging can be configured to allow a user to remove the device 105 from the packaging by grasping the plunger 145 and pulling on the plunger 145 to remove the device 105. In this way, the device 105 can be removed from the packaging using the plunger 145 without the device 105 becoming disassembled.

The device 105 can be inserted into the vaginal cavity by grasping the device 105 using the gripping area 120. In some embodiments, the gripping area 120 can include one or more protrusions 125 to aid a user in holding the device 105 for insertion into the vaginal cavity. The device 105 can be inserted into the vaginal cavity by holding the device via the gripping area, the plunger, the shell, or any combination thereof and pushing or otherwise advancing the device 105 into the vaginal cavity along the insertion axis 175.

At 420, the plunger 145 can be advanced within the shell 110 to cause the absorptive unit 170 to deploy within the vaginal cavity and to conform to a shape of the vaginal cavity. For example, with the device 105 inserted into the vaginal cavity, a user can hold the device 105 via the gripping area 120 and can advance the plunger 145 within the shell 110 to cause the plunger 145 to advance axially forward along the deployment axis 220. Advancing the plunger 145 in this manner can cause the absorptive unit 170 to be deployed within the vaginal cavity.

In some embodiments, for example, as shown in FIG. 2, the plunger 145 can be partially advanced within the shell 110 along the deployment axis 220. For example, the plunger 145 can be advanced to a first position at which the flexible stop 155 engages, abuts, or is positioned near the proximal end 115 of the shell 110. In this embodiment, the absorptive unit 170 can be partially deployed within the vaginal cavity. The absorptive unit 170 can be partially deployed from within the shell 110 by a user applying 0.54-0.73 kg-force to the plunger 145. When partially deployed from within the shell 110, the absorptive unit 170 can be configured to withstand 0.57-0.90 kg-force of lateral or perpendicular force without separating from the frame structure 210 and/or the plunger 145. The user can employ the device 105 in this partial deployment configuration to swab or manually maneuver the device 105 within the vaginal cavity to absorb fluids. The absorptive unit 170 can be partially deployed from within the shell 110 and into the vaginal cavity. The absorptive unit 170 can include expandable materials and/or the frame structure 210 to aid the absorptive unit 170 in partially deploying from the shell 110. For example, expansion of the absorptive unit 170 within the vaginal cavity can provide greater absorption of semen within the vaginal cavity compared to devices which do not include such features. The materials and components of the expandable absorptive unit 170 can cause the absorptive unit to conform to the anatomical features of the vaginal cavity. In this way, the device 105 can absorb vaginal fluids at greater rates of absorption in users with a broad range of vaginal anatomy and/or anatomical variability of the vaginal cavity.

In some embodiments, the method can further include retracting the absorptive unit 170 into the shell 110 by retracting the plunger 145 within the shell 110. For example, as shown in FIG. 2, the absorptive unit 170, which has been partially deployed, can be retracted into the shell 110 by pulling the plunger 145 along the retraction axis 225. The absorptive unit 170 can be retracted into the shell 110 by a user applying 0.57-0.90 kg-force to the plunger 145.

In some embodiments, for example, as shown in FIG. 3, the plunger 145 can be fully advanced within the shell 110 along the deployment axis 220. For example, with the device 105 inserted into the vaginal cavity, a user can hold the device 105 via the gripping area 120 and can advance the plunger 145 within the shell 110 to cause the plunger 145 to advance axially forward along the deployment axis 220. The plunger 145 can be advanced to a second position at which the flexible stop 155 is advanced past the proximal end 115 of the shell 110. For example, as shown in FIG. 3, the plunger 145 can be advanced such that the flexible stop 155 is positioned within the proximal end 115 of the shell 110. The plunger flange 160 located at the proximal end 150 of the plunger 145 can engage, abut, or otherwise be in proximity of the proximal end 115 of the shell 110. The plunger 145 can advanced to fully deploy the absorptive unit 170 from within the shell 110 by a user applying 0.54-0.73 kg-force to the plunger 145.

In the embodiment shown in FIG. 3, the absorptive unit 170 can be fully deployed within the vaginal cavity. The user can employ the device 105 in this full deployment configuration to position the absorptive unit 170 within the vaginal cavity to absorb semen for longer periods of time. For example, the absorptive unit 170 can be fully deployed from within the shell 110 and into the vaginal cavity when a user seeks to absorb semen without manually manipulating the device 105 as described in relation to the partial deployment configuration above.

When fully deployed within the vaginal cavity, the absorptive unit 170 can further expand to conform to the anatomical shape and geometries of the vaginal cavity. The expandable materials and/or frame structures 210 of the absorptive unit 170 aid fully deploying the absorptive unit from the shell 110 and within the vaginal cavity. Expansion of the absorptive unit 170 within the vaginal cavity can provide greater absorption of semen within the vaginal cavity compared to devices which do not include such features. The materials and components of the expandable absorptive unit 170 can cause the absorptive unit to conform to the anatomical features of the vaginal cavity. In this way, the device 105 can absorb semen at greater rates of absorption in users with a broad range of vaginal anatomy and/or anatomical variability of the vaginal cavity.

At 430, the absorptive element 205 of the absorptive unit 170 can absorb fluid present within the vaginal cavity. For example, the absorptive unit 170 and/or the absorptive elements 205 thereof can include a sponge material capable of absorbing semen from within the vaginal cavity. When the device 105 is used in the partial deployment configuration, semen can be absorbed in part due to user manipulation of the device to bring the absorptive unit 170 and/or the absorptive elements 205 into contact with semen present within the vaginal cavity. When the device 105, is used in the full deployment configuration, semen can be absorbed in part due to the absorptive unit 170 and/or the absorptive elements 205 interfacing more fully with anatomical features and semen within the vaginal cavity. The materials and components of the expandable absorptive unit 170 can enable higher rates of semen absorption from within the vaginal cavity, particularly when the absorptive unit 170 and/or the absorptive elements 205 are fully deployed and conforming to a larger percentage of the volume of the vaginal cavity.

In 440, the shell 110 and plunger 145 can be removed from the vaginal cavity. For example, following full deployment of the absorptive unit 170 described in relation to 420, the user may remove the shell 110 and the plunger 145 by grasping the gripping area 120 and/or a portion of the plunger 145 and retracting the shell 110 and the plunger 145 from the vaginal cavity. The shell 110 and the plunger 145 can be retracted, while leaving the absorptive unit 170 within the vaginal cavity, by withdrawing the shell 110 and the plunger 145 along the length of the tether 165 along a removal axis 320. The shell 110 and the plunger 145 can be configured as hollow structures including a lumen or inner passage therein (e.g., shell lumen 325 and plunger opening 310) to contain the tether 165. In this way, with the absorptive unit 170 positioned within the vaginal cavity, the shell 110 and the plunger 145 can slide around and along the tether 165 to be removed from the vaginal cavity along the removal axis 320.

In some embodiments, the method can further include removing the absorptive unit 170 from within the vaginal cavity by pulling the tether 165, the shell 110, the plunger 145, or any combination thereof. In some embodiments, as shown in FIG. 2, the absorptive unit 170, which has been partially deployed, can be removed from within the vaginal cavity by pulling the plunger 145, the shell 110, or a combination of the plunger 145 and the shell 110 along the retraction axis 225. In this example, the retraction axis 225 can also represent the removal axis 320, described in relation to FIG. 3 for withdrawing the device 105 and the absorptive unit 170 from within the vaginal cavity. When the absorptive unit 170 is in the full deployment configuration as shown in FIG. 3, the device 105 and the absorptive unit 170 can be removed from the vaginal cavity by pulling the tether 165. The device 105 can be discarded following removal from the vaginal cavity.

Figure 5:
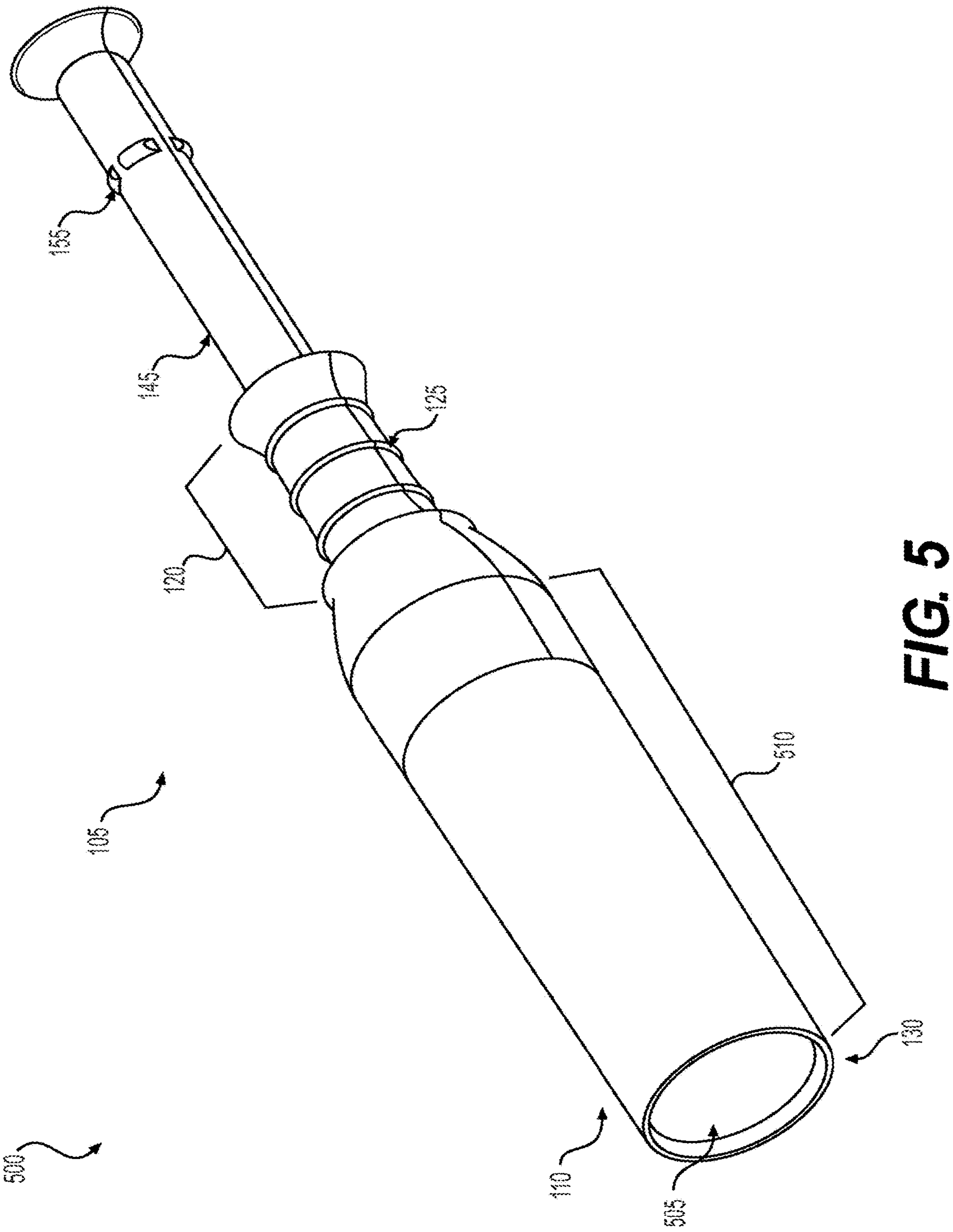
FIG. 5 is a diagram illustrating an isometric view of another exemplary embodiment of a device for vaginal fluid absorption and odor reduction according to some implementations of the current subject matter.

FIG. 5 is a diagram 500 illustrating an isometric view of another exemplary embodiment of a device 105 for vaginal fluid absorption and odor reduction according to some implementations of the current subject matter. The device 105 shown in FIG. 5 can include similar components and can perform similar functions as the device 105 shown and described in relation to FIGS. 1-3, except where noted otherwise. For example, the embodiment illustrated in FIG. 5 can include a shell 110 which does not include a flexible head at the distal end 130.

As shown in FIG. 5, the distal end 130 of the shell 110 can include an opening 505 through which the absorptive unit can be released from within the shell 110. The shell 110 can be formed with a slight taper extending from about the gripping area 120 to the distal end 130 as shown in the tapered area 510. The opening 505 can be formed of geometry and dimensions corresponding to the tapered area 510. In some embodiments, the opening 505 can be configured to control the deployment of the absorptive unit 170 from within the shell 110. In some embodiments, the opening 505 can be configured to retain the absorptive unit 170 within the shell 110 prior to deployment or following retraction of the absorptive unit into the shell 110. The opening 505 and the tapered area 510 can be configured as atraumatic components, which can reduce the likelihood of tissue damage or trauma when inserting the device 105 into the vaginal cavity or when deploying the absorptive unit 170 within the vaginal cavity.

Figure 6:
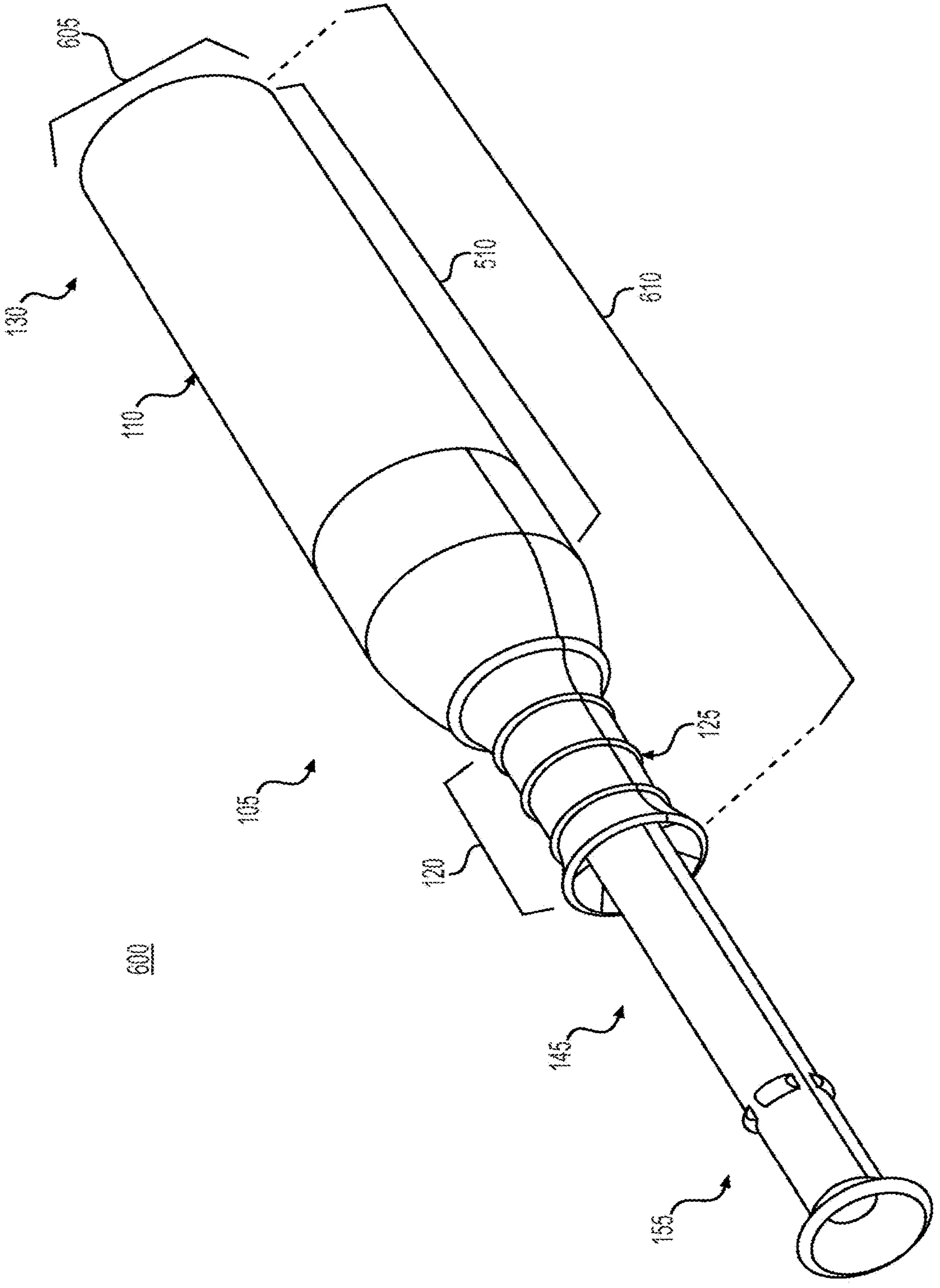
FIG. 6 is a diagram illustrating a reverse isometric view of the exemplary embodiment of the device shown in FIG. 5.

FIG. 6 is a diagram illustrating a reverse isometric view of the exemplary embodiment of the device shown in FIG. 5. As shown in FIG. 6, the shell 110 can include a diameter 605 that can be between 1.5 cm-2.3 cm. In embodiments described herein, the diameter 605 of the shell 110 can be 1.9 cm. The shell 110 can include a length 610 that can be between 7.5 cm-10.2 cm. In embodiments described herein, the length 610 of the shell 110 can be 9.1 cm. In embodiments described herein the device 105 can weigh between 3.15 grams and 5.45 grams. In some embodiments, the device 105 can weigh 1.5 grams.

Figure 7:
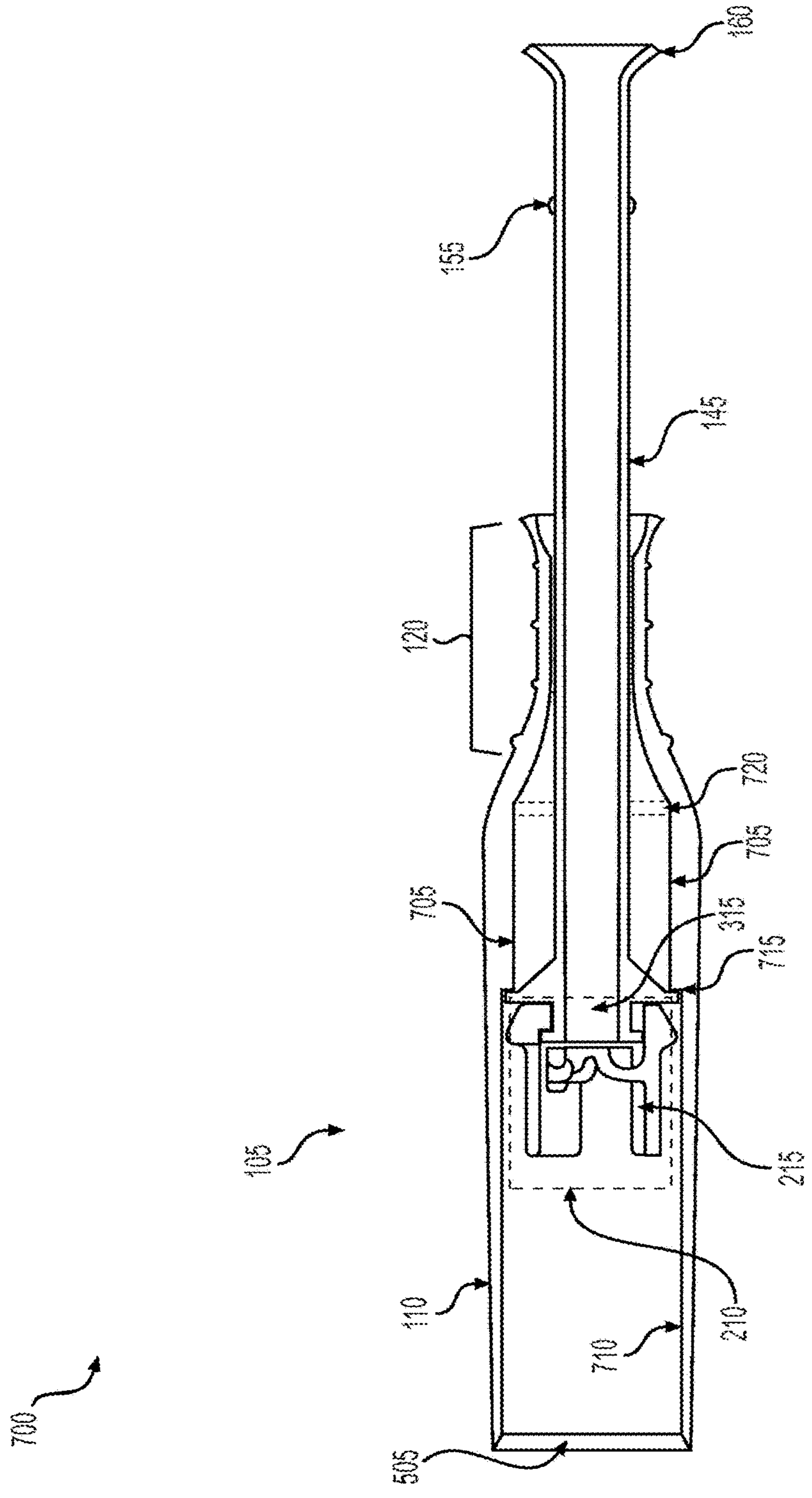
FIG. 7 is a diagram illustrating a cross-sectional view of an exemplary embodiment of the device shown in FIG. 5.

FIG. 7 is a diagram 700 illustrating a cross-sectional view of the exemplary embodiment of the device 105 shown in FIG. 5. The device 105 shown in FIG. 7 includes similar components and performs similar functions as the device 105 shown and described in relation to FIG. 5, except where noted otherwise. The embodiment of the device 105 shown in FIG. 7 is shown with the plunger 145 in a retracted position and without an absorptive unit so that the frame structure 210 shown within the dashed-line box can be more readily visualized.

As shown in FIG. 7, the frame structure 210 can include a plurality of frame structure extensions 215 extending from a base portion of the frame structure. The frame structure 210 can be affixed to the distal end 315 of the plunger 145. The shell 110 can include a plurality of ribs 705 configured on an interior surface 710 of the shell 110. The ribs 705 can provide structural rigidity to the shell 110 and can reduce torsional deformation of the shell 110. The ribs 705 can originate proximate to the gripping area 120 and can extend partially along the interior surface 710 of the shell 110 in an axial direction toward the opening 505. The distal end 715 of the ribs 705 can engage the distal end 315 of the plunger 145 to limit the stroke of the plunger 145 within the shell 110. In this way, the distal end 715 of the ribs 705 can provide a backstop when the plunger 145, frame structure 210, and the absorptive unit are retracted into the shell 110. As further shown in FIG. 7, the interior surface 710 can also include one or more concentric ridges 720 extending circumferentially around the interior surface 710 of the shell 110. A plurality of concentric ridges 720 can telescopically extend along the interior surface 710 toward the opening 505 of the shell 110. Concentric ridges 720 can provide structural support to the shell 110 during assembly and use.

Figure 8:
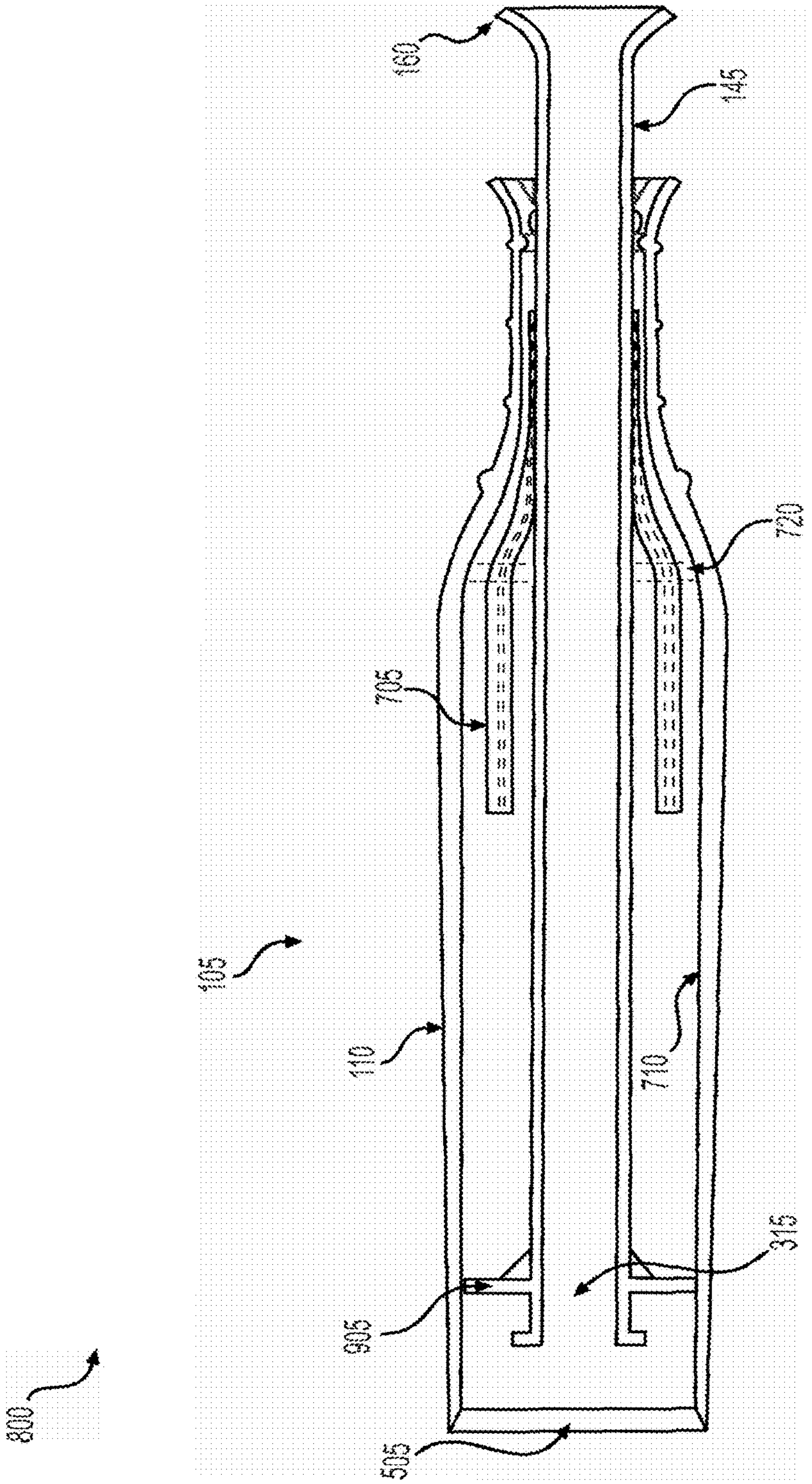
FIG. 8 is diagram illustrating another cross-sectional view of an exemplary embodiment of the device shown in FIG. 5.

FIG. 8 is diagram 800 illustrating another cross-sectional view of an exemplary embodiment of the device 105 shown in FIG. 5. In FIG. 8, the device 105 is shown with the plunger 145 in a partially deployed configuration. In FIG. 8, the device 105 is shown without an absorptive unit, such as absorptive unit 205 shown in FIGS. 2-3, and without a frame structure, such as frame structure 210 shown in FIGS. 2 and 7. In this way, the ribs 705 and portions of the distal end 315 of the plunger 145 can be more readily visualized.

The ribs 705 can be formed of the same material as the shell 110. In some embodiments, 2, 3, 4, 5, 6, 7, 8, 9, or 10 ribs 705 can be configured circumferentially on the interior surface 710 of the shell 110. The length of the ribs 705, measured from a portion of the gripping area 120 to the opening 505, can be configured to correspond to the size of the absorptive unit, such as absorptive unit 205 shown in FIGS. 2-3, and/or the frame structure, such as frame structure 210 shown in FIGS. 2 and 7. In some embodiments, each of the ribs 705 can be configured with a height between about 0.3 mm and about 1.0 mm. The height of each rib 705 can be measured as extending away from the interior surface 710 of the shell 110 to a point on the rib 705 farthest away from the interior surface 710 of the shell 110. The height of each rib 705 can vary along the length of the rib. For example, a given rib 705 can have a height of about 0.875 mm at the distal end 715 of the rib 705 and a thickness of about 0.4 mm at a proximal end of the rib 705 closest to the concentric ridge 720. In this way, the rib 705 can be tapered along its length and can have a length about 2.5-4.0 cm. In some embodiments, the length of each rib 705 can correspond to the length of the absorptive unit 170. In some embodiments, the height of each rib 705 can be about the same as the nominal wall thickness of the shell 110.

Figure 9:
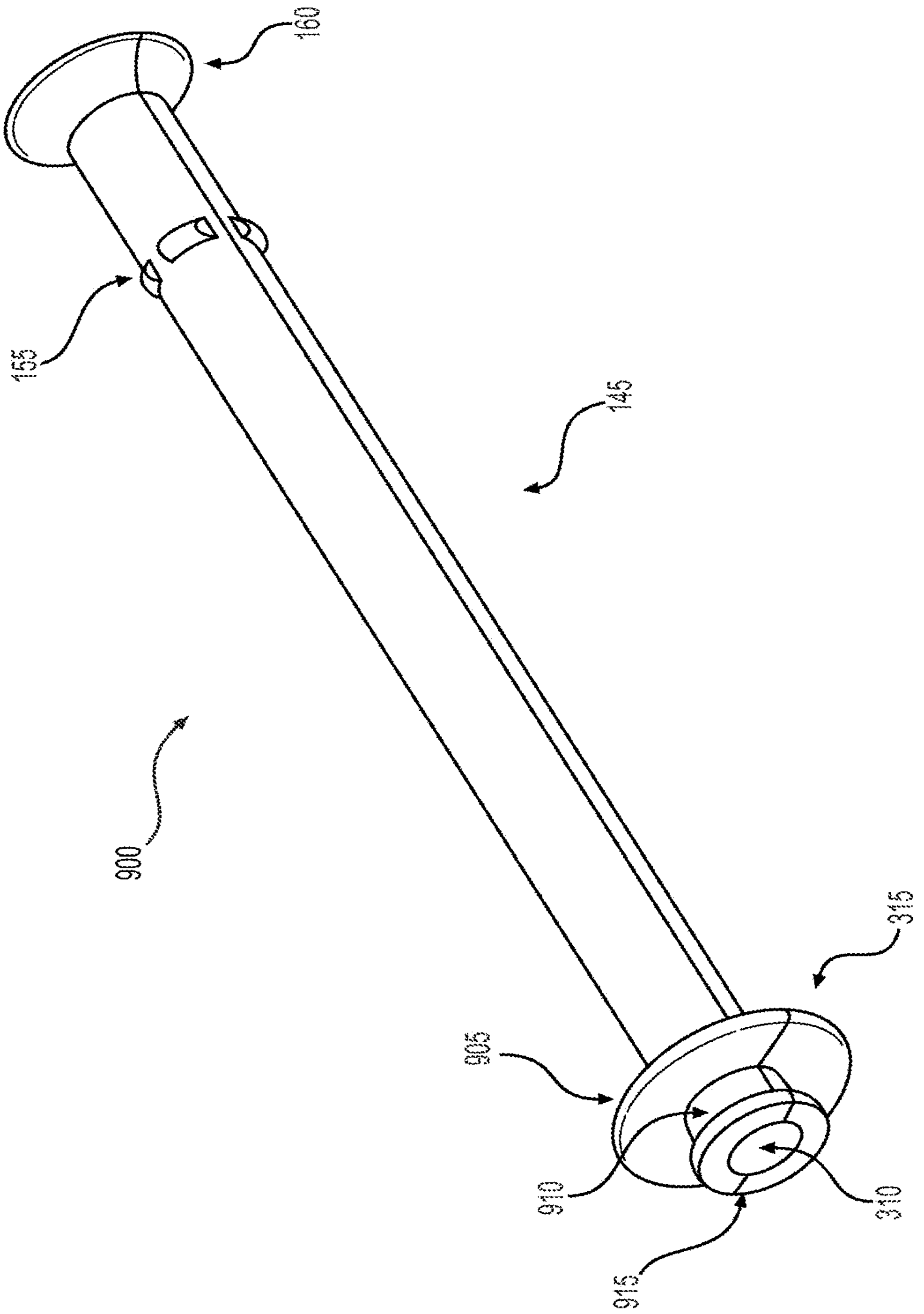
FIG. 9 is a diagram illustrating an isometric view of an exemplary embodiment of a plunger of a device for vaginal fluid absorption and odor reduction according to some implementations of the current subject matter.

FIG. 9 is a diagram 900 illustrating an isometric view of an exemplary embodiment of a plunger 145 of a device 105 for vaginal fluid absorption and odor reduction according to some implementations of the current subject matter. As shown in FIG. 9, the distal end of the plunger 145 can include an opening 310 located at the distal end 315 of the plunger 145. The opening 310 can convey one or more tethers, such as tethers 165 shown in FIG. 3, from the frame structure 210 and through the plunger flange 160.

As shown in FIG. 9, the distal end 315 of the plunger 145 can include an abutment element 905, a support element 910, and a coupling mechanism 915. The abutment element 905 can be a disc-shaped element that is configured to abut or interface with lower portions of the frame structure, such as the frame structure 210 shown in FIG. 7. The abutment element 905 can provide a structural base for the frame structure 210 during deployment of the absorptive unit 170 from within the shell 110. The diameter of the abutment element 905 can be sized such that it can interface to the inner surface of the shell 110, as shown in FIG. 8. Thus, the abutment element 905 can be friction fit within the shell 110 such that deflection of the distal end 315 of the plunger 145 with respect to the deployment axis of the shell 110 can be reduced or eliminated, yet rotation of the plunger 145 within the shell 110 can still occur.

As further shown in FIG. 9, the support element 910 can extend from the abutment element 905 and can include a height suitable for receiving portions of the frame structure 210. The coupling mechanism 915 can sit atop the support element 910 and can be configured as a disc-shaped element surrounding the plunger opening 310. The coupling mechanism 915 can be configured with a diameter and thickness suitable to secure the frame structure 210 thereto.

Figure 10:
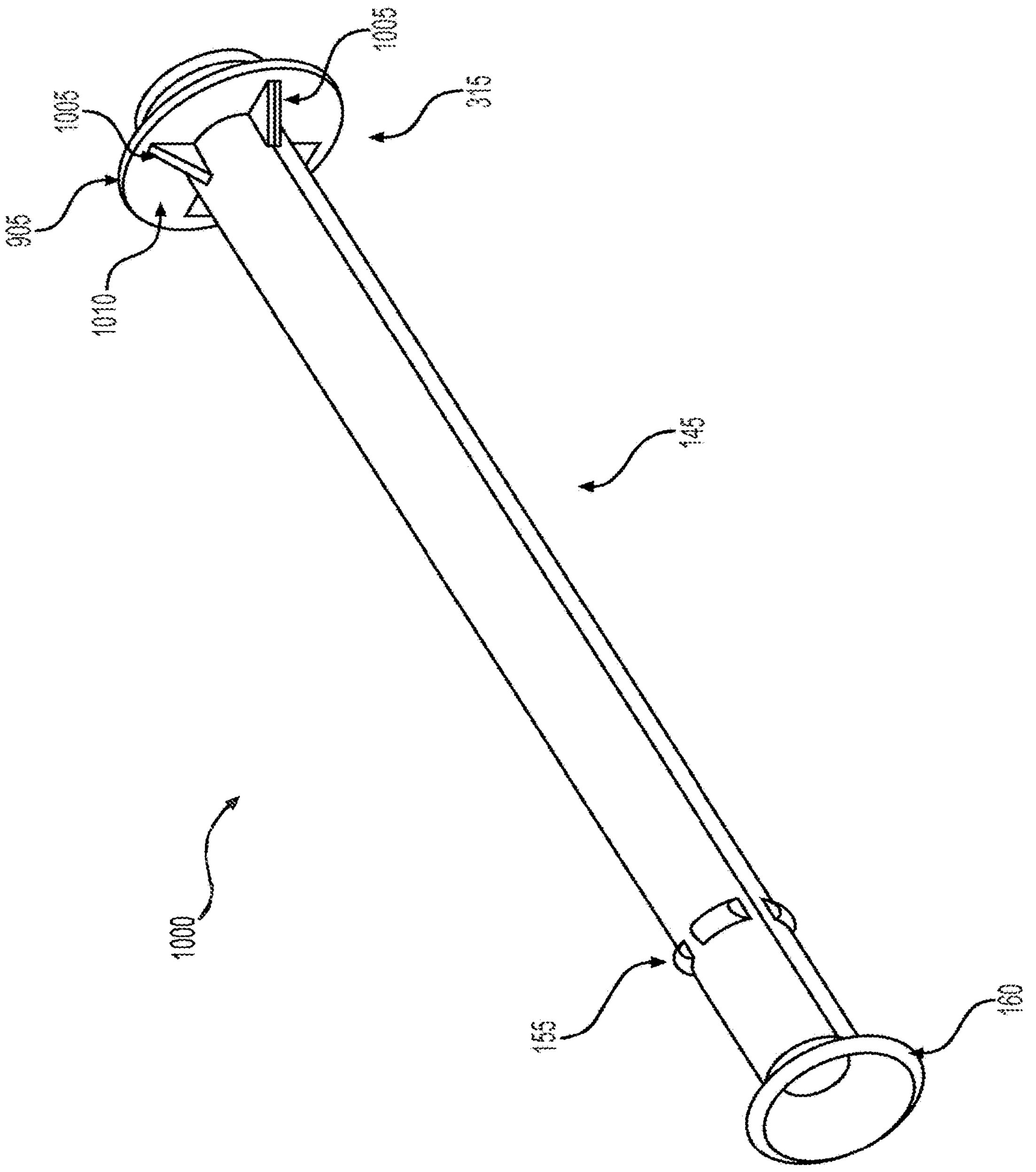
FIG. 10 is a diagram illustrating a reverse isometric view of the exemplary embodiment of the plunger shown in FIG. 9.

FIG. 10 is a diagram 1000 illustrating a reverse isometric view of the exemplary embodiment of the plunger 145 shown in FIG. 9. As shown in FIG. 10, the abutment element 905 can include one or more abutment element supports 1005. The abutment element supports 1005 can secure the abutment element 905 to the plunger 145 and can provide structural support for the abutment element 905. Although the abutment element supports 1005 are shown in an angular-shaped configuration, the abutment element supports 1005 can also be configured in a ring-shape. In some embodiments, the abutment element support 1005 can be fluted-shape or cone-shape, in which a continuous portion of material extends from the distal end of the plunger to surface 1010 of the abutment element 905.

Figure 11:
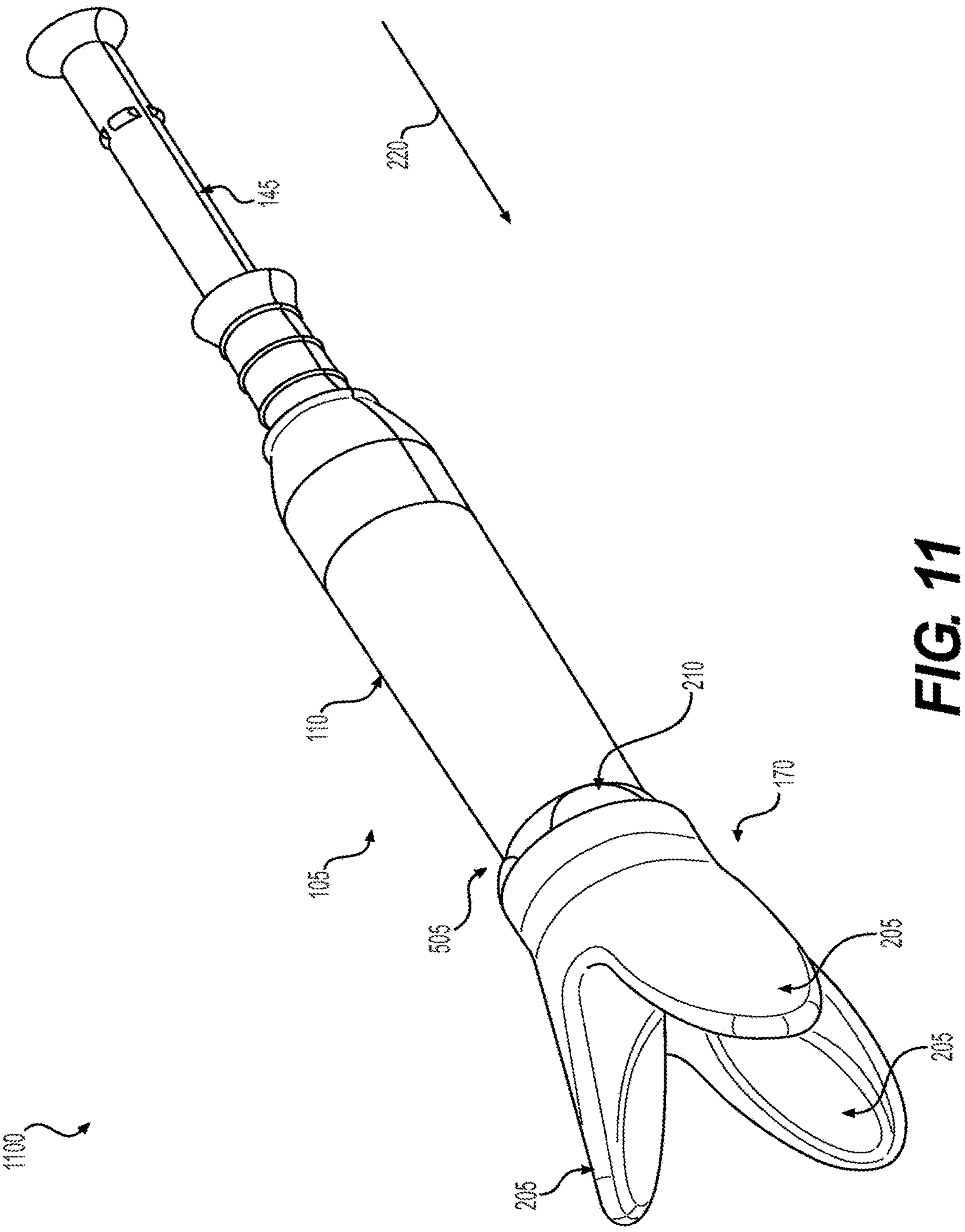
FIG. 11 is a diagram illustrating an isometric view of another exemplary embodiment of a device for vaginal fluid absorption and odor reduction according to some implementations of the current subject matter.

FIG. 11 is a diagram 1100 illustrating an isometric view of another exemplary embodiment of a device 105 for vaginal fluid absorption and odor reduction according to some implementations of the current subject matter. The device 105 can include similar components and perform similar functions as the device 105 described in relation to FIGS. 1-3, and 5-8, except where noted otherwise. The device 105 in FIG. 11 is shown in a partially deployed configuration such that the absorptive unit 170 has been advanced from within the shell 110 and through the opening 505. The plurality of absorptive elements 205 have expanded from their compressed configuration within the shell 110 due to the partial deployment achieved by advancing the plunger 145 within the shell 110 along the deployment axis 220.

Figure 12:
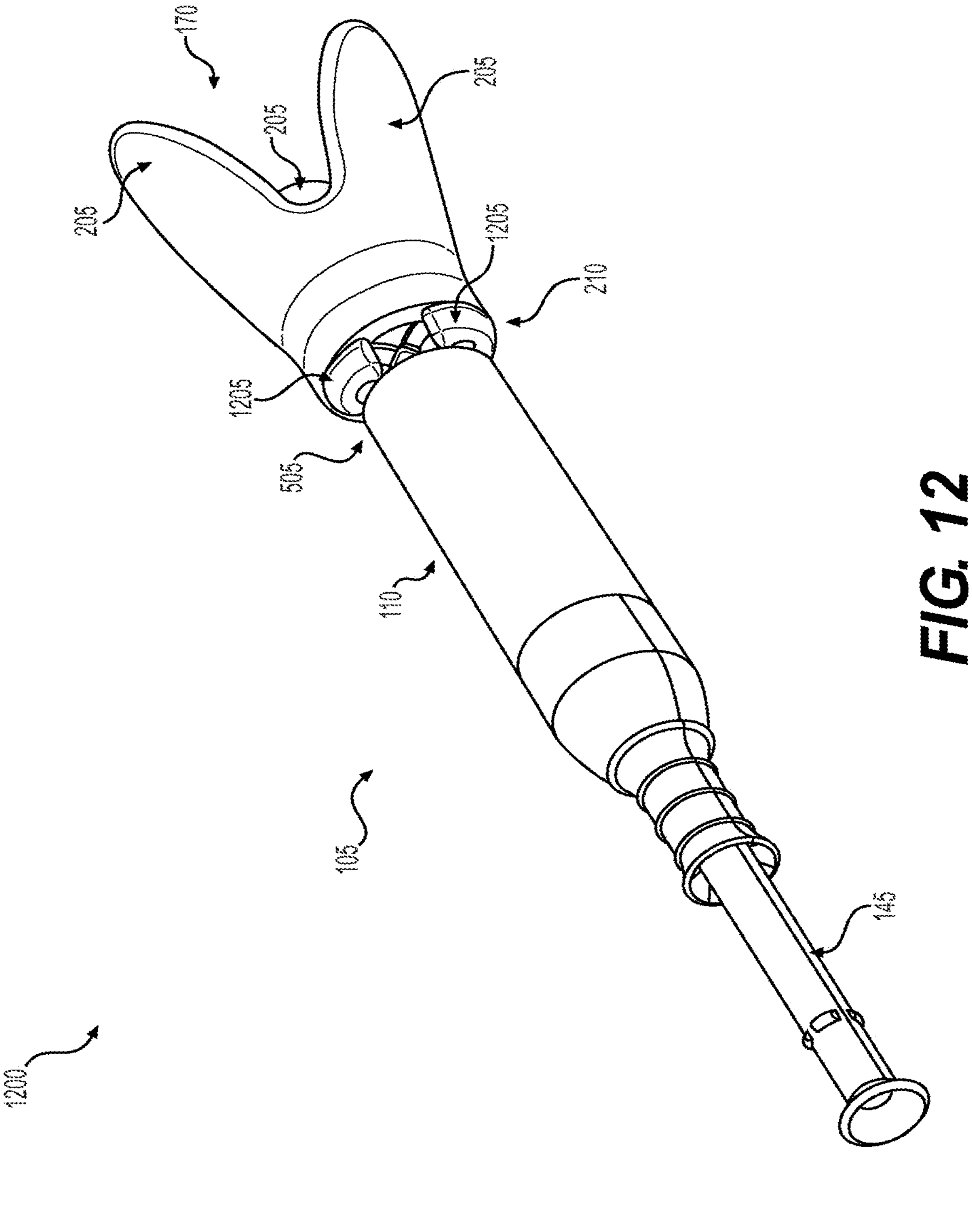
FIG. 12 is a diagram illustrating a reverse isometric view of the exemplary embodiment of the device shown in FIG. 11.

FIG. 12 is a diagram 1200 illustrating a reverse isometric view of the exemplary embodiment of the device 105 shown in FIG. 11. As shown in FIG. 12, the absorptive unit 170, including the plurality of absorptive elements 205 and the frame structure 210, has been advanced from within the shell 110 via the opening 505. The frame structure 210 can include a plurality of frame structure segments 1205, which will be described in further detail later.

Figure 13:
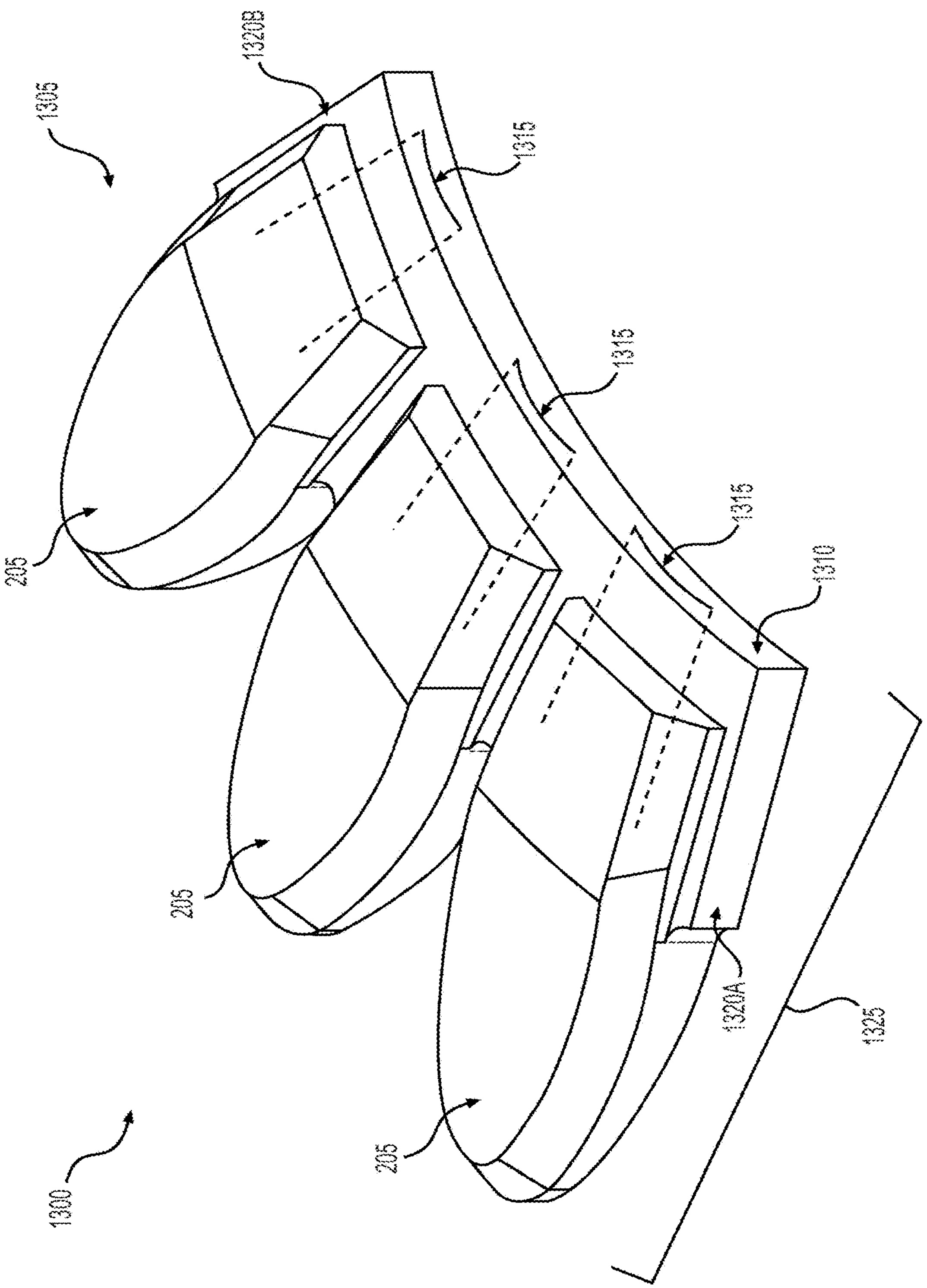
FIG. 13 is a diagram illustrating an isometric view of an exemplary embodiment of a portion of an absorptive unit of a device for vaginal fluid absorption and odor reduction according to some implementations of the current subject matter.

FIG. 13 is a diagram 1300 illustrating an isometric view of an exemplary embodiment of a portion of an absorptive unit 1305 of a device 105 for vaginal fluid absorption and odor reduction according to some implementations of the current subject matter. As shown in FIG. 13, the absorptive unit 1305 can be formed from a single piece of sponge 1310, such as polyurethane sponge. In some embodiments, the sponge 1310 can be a flat piece of stock sponge that is cut to form a plurality of absorptive elements 205 as described in relation to FIG. 2 and as shown in FIG. 13. The configuration of the absorptive element 1305 shown in FIG. 13 corresponds to a pre-assembly configuration in which the plurality of the absorptive elements 205 are formed. A plurality of cutouts or pockets 1315 can be formed within the sponge 1310 and can extend through the corresponding absorptive elements 205 as shown by dashed lined extending from each cutout 1315. The cutouts 1315 can be configured to receive a frame structure extension 215 shown in FIG. 7 and will be described later. The cutouts 1315, the absorptive unit 170, and absorptive elements 205 can be formed via contour cutting, die cutting, laser cutting, hot wire cutting, or any combination thereof. The dimensions, shapes, and overall configuration of the cutouts 1315 within the absorptive elements 205 can be configured to enable maximal deployment of the absorptive elements 205 from a compressed state within the shell 110 prior to usage of the device 105. As a result, the absorptive unit 170, as shown in regard to FIGS. 11 and 12 can better conform to the anatomical shape of the vaginal cavity and thereby enhance fluid absorption.

During assembly of the absorptive unit 170, the edges 1320A and 1320B can be joined to form a three-dimensional absorptive unit with a circular base and the absorptive elements 205 extending from the circular base. The edges 1320A and 1320B can be joined using biodegradable glue or using radio-frequency (RF) welding. In RF welding, the material of the sponge 1305 located at the edges 1320A and 1320B is energized and melted causing the edges 1320A and 1320B to fuse together to form the three-dimensional absorptive unit 170, as shown in regard to FIGS. 11 and 12. Each absorptive element 205 can include a length 1325 measured from a tip of an absorptive element 205 to a base of the absorptive element 205. A frame structure extension can be received in the cutouts 1315 located at the base of each absorptive element 205.

Figure 14B:
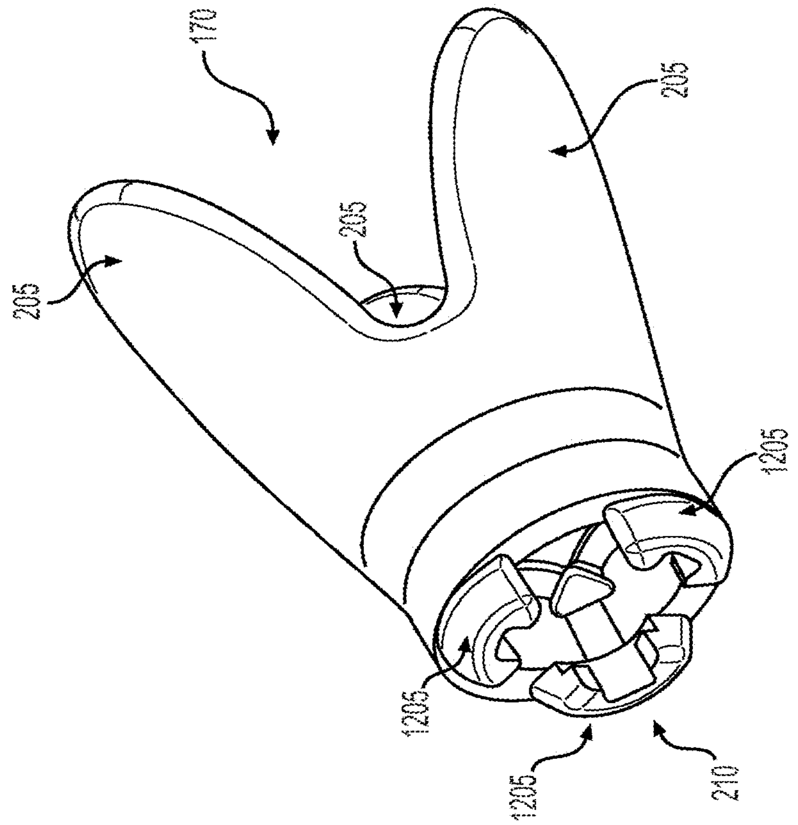
FIG. 14B is a diagram illustrating a reverse isometric view of the exemplary embodiment of the absorptive unit shown in FIG. 14A.
Figure 14A:
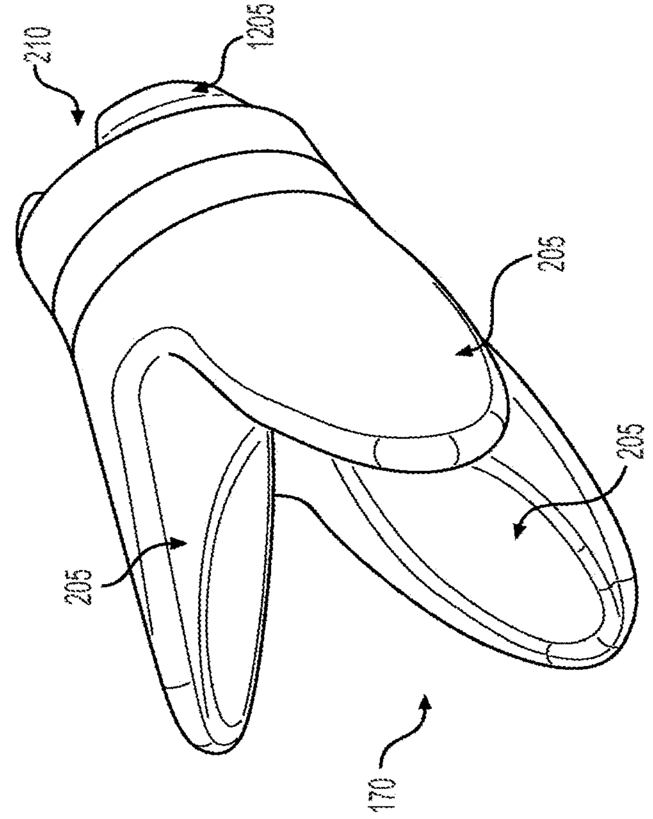
FIG. 14A is a diagram illustrating an isometric view of an exemplary embodiment of an absorptive unit of a device for vaginal fluid absorption and odor reduction according to some implementations of the current subject matter.

FIG. 14A is a diagram illustrating an isometric view of an exemplary embodiment of an absorptive unit 170 of a device for vaginal fluid absorption and odor reduction according to some implementations of the current subject matter. The absorptive unit 170 as shown in FIG. 14A can be formed from the sponge 1305 and method described in relation to FIG. 13. Once formed, the frame structure 210 can be inserted into the cutouts 1315 such that frame structure extensions, such as the frame structure extensions 215 shown in FIGS. 2-3, and 7, can be positioned within each of the cutouts 1315. The frame structure extensions 215 can be secured within the cutouts 1315 via biodegradable glue or RF welding. The frame structure 210 can include one or more frame structure segments 1205

FIG. 14B is a diagram illustrating a reverse isometric view of the exemplary embodiment of the absorptive unit 170 shown in FIG. 14A. As shown in FIG. 14B, the frame structure 210 includes a plurality of frame structure segments 1205. In some embodiments, the absorptive unit 170 can include 1, 2, 3, 4, 5, 6, 7, 8, or more frame structure segments 1205. One or more frame structure extensions 215 can be included in each frame structure segment 1205. The plurality of frame structure segments 1205 can be coupled to each other via one or more linkages or spokes as shown in FIG. 14B to form a unibody frame structure 210.

Figure 15:
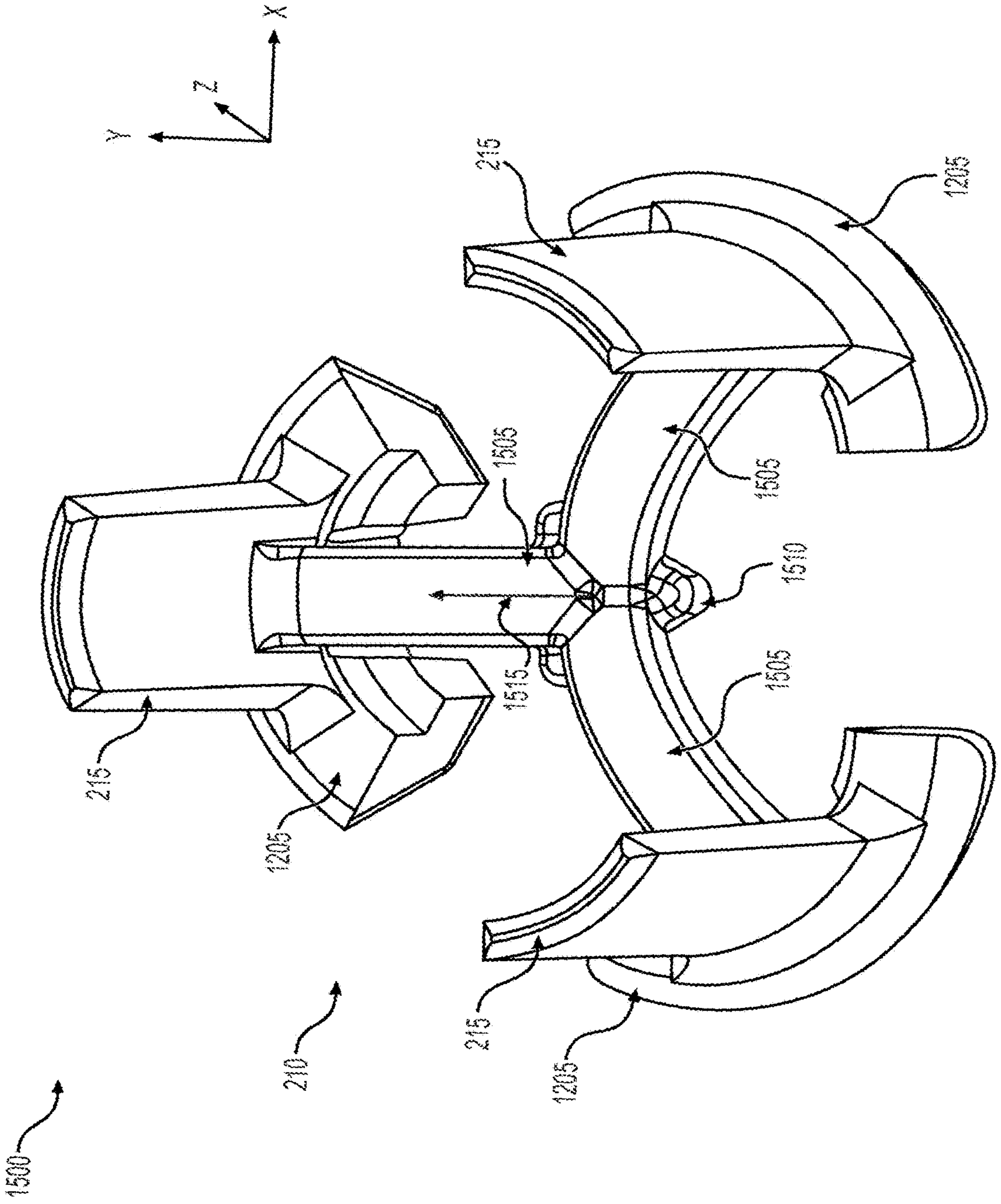
FIG. 15 is a diagram illustrating an isometric top view of an exemplary embodiment of a frame structure of a device for vaginal fluid absorption and odor reduction according to some implementations of the current subject matter.

FIG. 15 is a diagram 1500 illustrating an isometric top view of an exemplary embodiment of a frame structure 210 of a device 105 for vaginal fluid absorption and odor reduction according to some implementations of the current subject matter. The frame structure 210 can be formed of thermoplastic elastomer or thermoplastic polyurethane via injection. In some embodiments, the frame structure 210 can include a polyester material. The frame structure material can have a durometer of about 70, as measured on the Shore A durometer scale. The frame structure 210 shown in FIG. 15 depicts the frame structure as molded and prior to insertion within an absorptive unit 170.

As shown in FIG. 15, the plurality of frame structure segments 1205 can be coupled to one another via a plurality of segment spokes 1505 and a hub 1510. The segment spokes 1505 can be configured as an arch-shaped structure linking the hub 1510 with each of the frame segments 1205. Although the frame structure 210 shown in FIG. 15 is depicted with three frame segments 1205 and a corresponding number of segment spokes 1505, more or less numbers of frame segment 1205 and segment spokes 1505 can be envisioned without limitation. In some embodiments, the segment spokes 1505 can include a rectangular cross-section. In some embodiments, the segment spokes 1505 can include a circular, oval, or square cross-section. The hub 1510 can be coupled to each of the segment spokes 1505 as shown in FIG. 15. In some embodiments, the hub 1510 can include a triangular shape. In some embodiments, the hub 1510 can include a circular, oval, or square shape.

As will be described in more detail later, the segment spokes 1505 can be configured to flex due to the elastic nature of the frame structure 210 material. This flexion can allow the segment spokes 1505 and the hub 1510 to travel vertically relative to the Y-axis shown in FIG. 15 in an upwards or downward motion. The Y-axis can be considered to be the same as the vertical axis 1515 extending upward from the hub 1510 in FIG. 15. The vertical flexion upward or downward of the segment spokes 1505 and the hub 1510 provides a means of transitioning the frame segments 1205 from an uncompressed configuration, as shown in FIG. 15, to a compressed configuration in which the frame segments 1205 are more closely coupled. The uncompressed configuration can correspond to an as-molded configuration of the frame structure 210, as well as a fully deployed configuration of the device 105 in which the frame structure 210 has been released fully from the shell 110 during use. The compressed configuration can correspond to an assembled configuration of the device 105 in which the frame structure 210 is inserted into the absorptive unit 170 prior to use, as well as a partial deployment configuration of the device 105 in which the frame structure 210 has not been released fully from the shell 110 during use.

Figure 16:
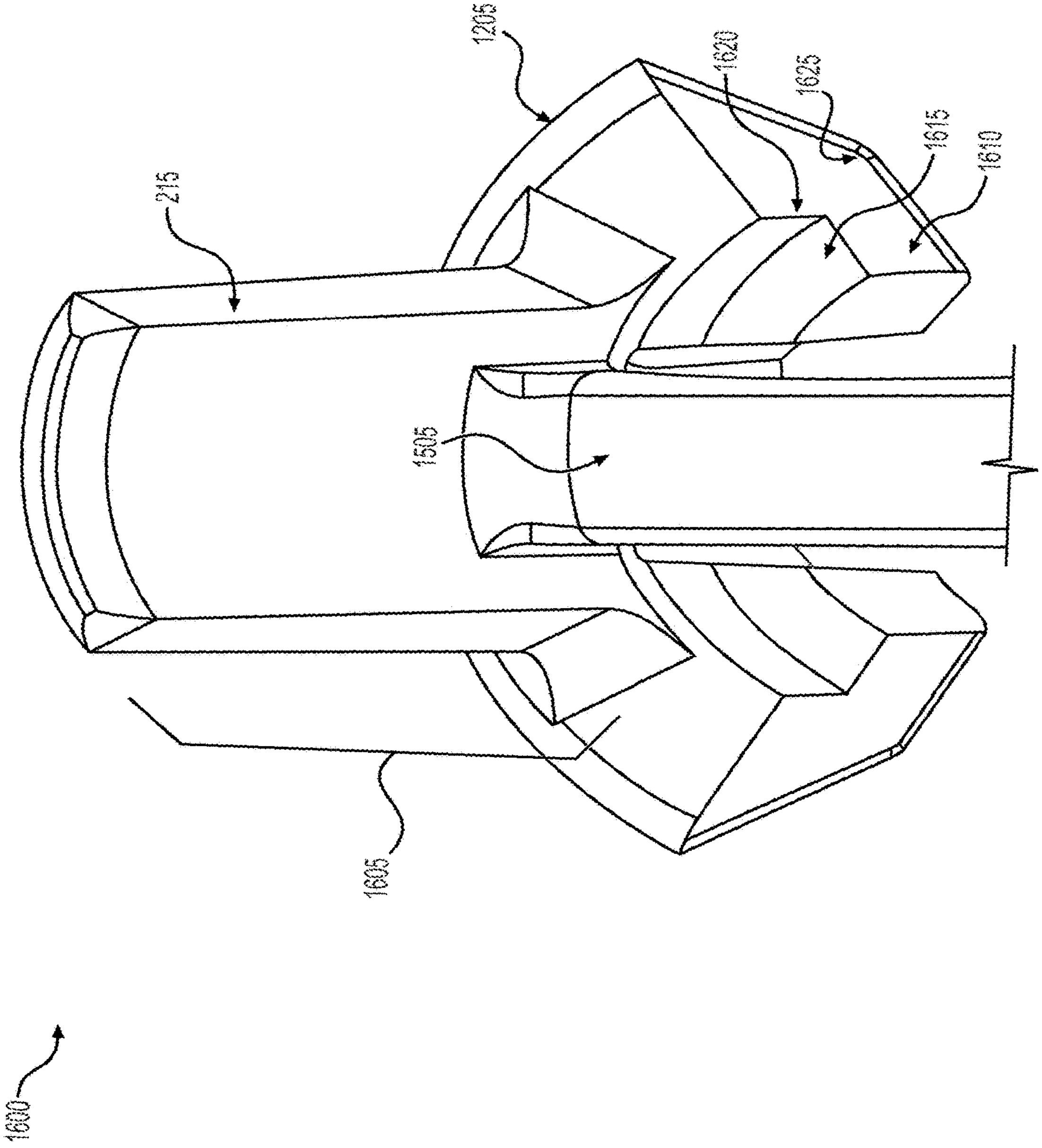
FIG. 16 is a diagram illustrating an exploded isometric top view of a frame segment of the exemplary embodiment of the frame structure shown in FIG. 15.

FIG. 16 is a diagram 1600 illustrating an exploded isometric top view of a frame segment 1205 of the exemplary embodiment of the frame structure 210 shown in FIG. 15. As shown in FIG. 16, the frame structure extension 215 can have a height 1605. The height 1605 can be configured relative to the depth of the cutouts 1315 shown in FIG. 13, as well as the configuration of the absorptive elements 205. The height 1605 can be between 1- and 3.0 cm, although other heights are possible. In some embodiments, the height can be greater than 3.0 cm or less than 1.0 cm. The height 1605 can enable the frame structure extensions 215 to extend into an absorptive element 205, such as the absorptive elements 205 shown in FIG. 13. In some embodiments, a frame structure extension 215 can extend into an absorptive element 205 to a distance that is 25-90% of a length of the absorptive element 205. The height 1605 and shape of the frame structure extension 215 can enhance the ability of the absorptive elements 205 to unfold within the vaginal cavity.

The absorptive elements 205 can be compressed to less than 50% of their original size when assembled within the shell 110 prior to partial or full deployment. The absorptive elements 205 can be configured to unfold, upon full deployment, to 90-95% of their original size. The original size of the absorptive elements 205 can correspond to a size of the absorptive elements 205 prior to their assemblage and insertion into the shell 110. In some embodiments, the frame structure extensions 215 can include additional extending portions, which can be coupled to the frame structure extensions 215 to enhance the ability of the absorptive unit 170 to retain its shape when deployed from within the shell 110. In addition, the material properties of the absorptive elements 205 enable the absorptive unit 170 to expand when the absorptive elements 205 become wet and absorb fluid within the vaginal cavity. In this way, the actuation of segment spoke 1515 relative to the hub 1510 can be enhanced to aid opening of the absorptive unit when deployed from the shell 110.

As further shown in FIG. 16, the frame segment 1205 can include a flange 1610 extending from the lower portion of the frame segment 1205 toward the center of frame segment 1205 (e.g., toward the hub 1510). The flange 1610 includes an upper surface 1615 at which the coupling mechanism 915 of the plunger 145, as shown in FIG. 9, can be received. The frame segment 1205 can include a collar portion 1620 to secure the coupling mechanism 915 of the plunger 145 on the upper surface 1615 of the flange 1610. The height of the collar portion 1620 can correspond to a thickness of the coupling mechanism 915 of the plunger 145. The lower surface 1625 of the frame segment 1205 can interface with the abutment element 905 of the plunger 145 shown in FIG. 9. The coupling configuration between the abutment element 905 and the coupling mechanism 915 with the lower surface 1625 of the frame segment 1205 and the upper surface 1615 of the flange 1610, respectively, can provide enhanced structural rigidity of the device 105 during deployment and retraction of the absorptive unit 170 via user operation of the plunger 145.

Figure 17:
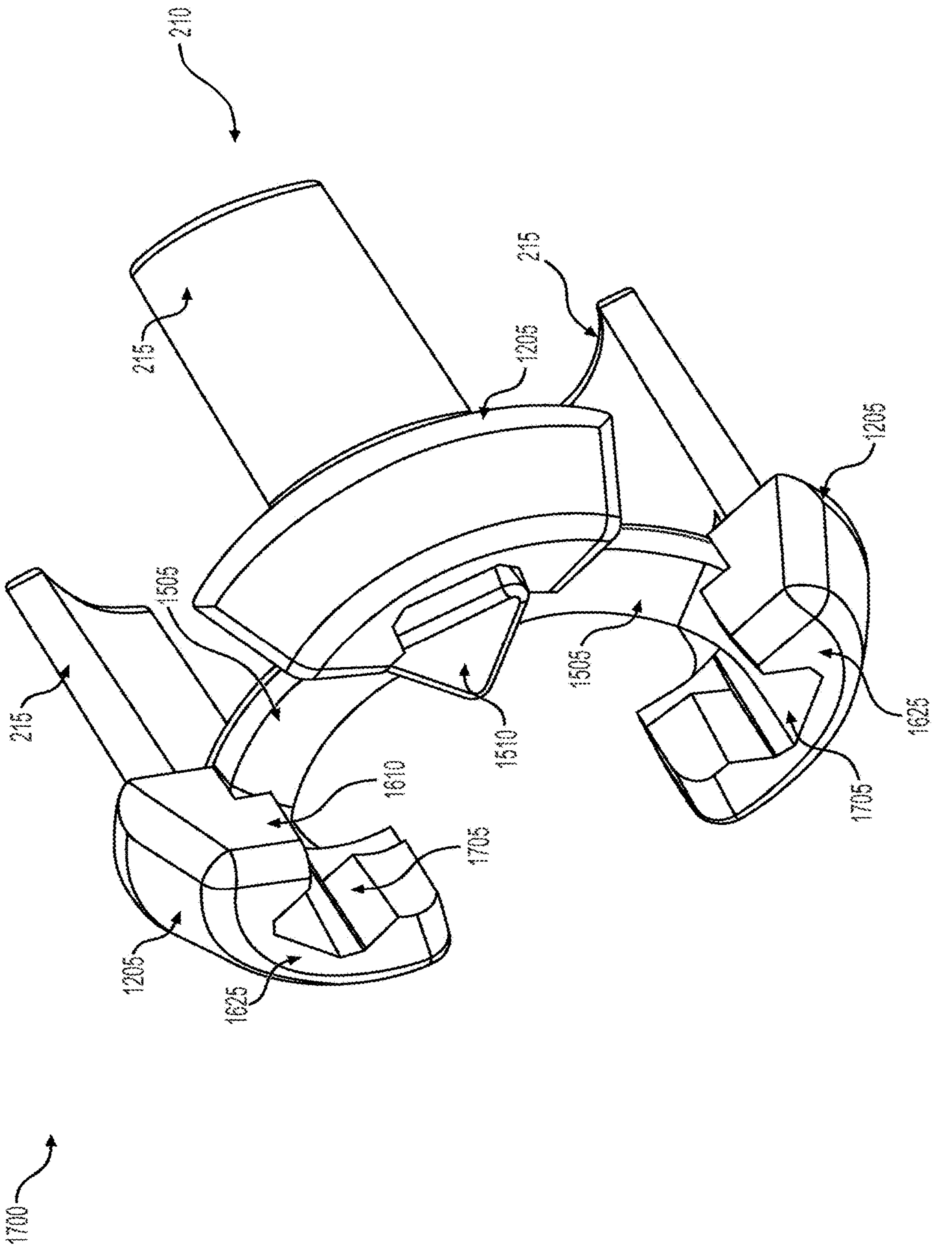
FIG. 17 is a diagram illustrating an isometric bottom view of the exemplary embodiment of the frame structure shown in FIG. 15.

FIG. 17 is a diagram 1700 illustrating an isometric bottom view of the exemplary embodiment of the frame structure 210 shown in FIG. 15. As shown in FIG. 17, frame segments 1205 can include a cutaway portion 1705 extending from the lower surface 1625 of the frame segment 1205. The cutaway portion 1705 can enable the segment spokes 1505 to flex in an upward or downward direction as described in relation to FIG. 15.

Figure 18:
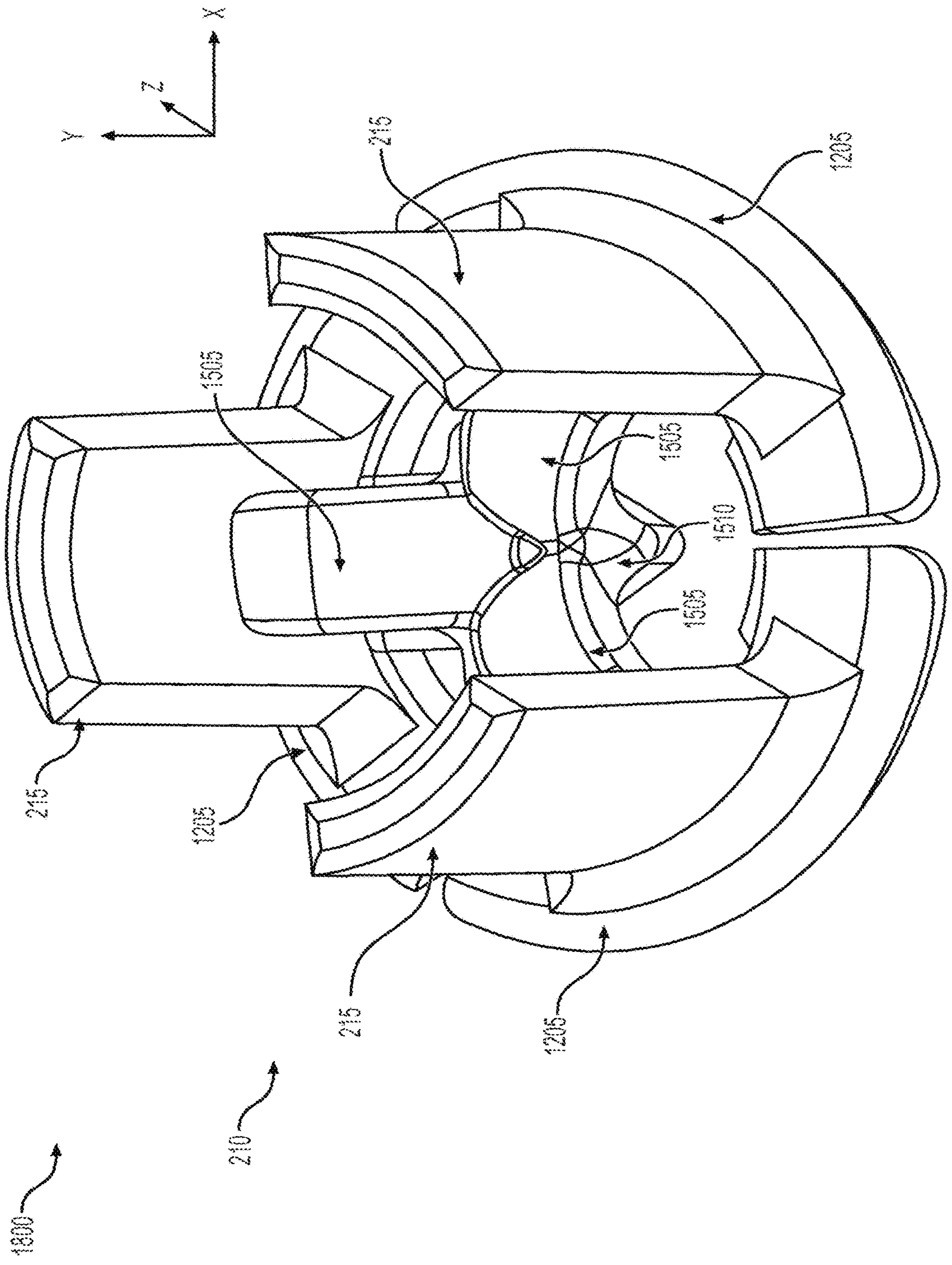
FIG. 18 is a diagram illustrating an isometric top view of another exemplary embodiment of the frame structure shown in FIG. 15.

FIG. 18 is a diagram 1800 illustrating an isometric top view of another exemplary embodiment of the frame structure 210 shown in FIG. 15. The frame structure 210 is shown in a compressed configuration compared to the uncompressed configuration of the frame structure in FIG. 15. The compressed configuration shown in FIG. 18 is achieved due to the materials and design of the frame structure 210, and specifically the configuration of the segment spokes 1505 and hub 1510. For example, the flexible segment spokes 1505 can accommodate pressure applied to the frame segments 1205 causing them to transition from an uncompressed configuration as shown in FIG. 15 to the compressed configuration shown in FIG. 18. Such a transition can be required when assembling the device 105, for example, when inserting the frame structure 210 into the plurality of absorptive elements 205. Transition from the uncompressed configuration shown in FIG. 15 to the compressed configuration shown in FIG. 18 can also be required when retracting the absorptive unit 170 back into the shell 110 following partial or fully deployment during use.

Transition from the compressed configuration shown in FIG. 18 to the uncompressed configuration shown in FIG. 15 can similarly be achieved due to the materials and design of the frame structure 210, and specifically the configuration of the segment spokes 1505 and hub 1510. For example, during some aspects of partial deployment, the frame structure 210 can be released from the shell 110. The segment spokes 1505 can expand away from the hub 1510 when the frame segments 1205 are no longer confined within the shell 110 and the frame structure 210 can transition from the compressed configuration shown in FIG. 18 to a uncompressed configuration shown in FIG. 15. During full deployment of the device 105 within the vaginal cavity, the absorptive unit 170 would be displaced from the shell 170 allowing the frame structure 210 to expand from the compressed configuration shown in FIG. 18 to the uncompressed configuration shown in FIG. 15. The ability of the frame structure 210 to transition from the compressed configuration to the uncompressed configuration enables the absorptive unit 170 to expand deeper into the remote regions of the vaginal cavity, such as the vaginal apex and fornixes. Engaging the absorptive unit 170 with these portions of the vaginal cavity using the device 105 and the frame structure 210 described herein can increase semen absorption and reduce vaginal odor in the vaginal cavity compared to existing methods and devices.

Figure 19:
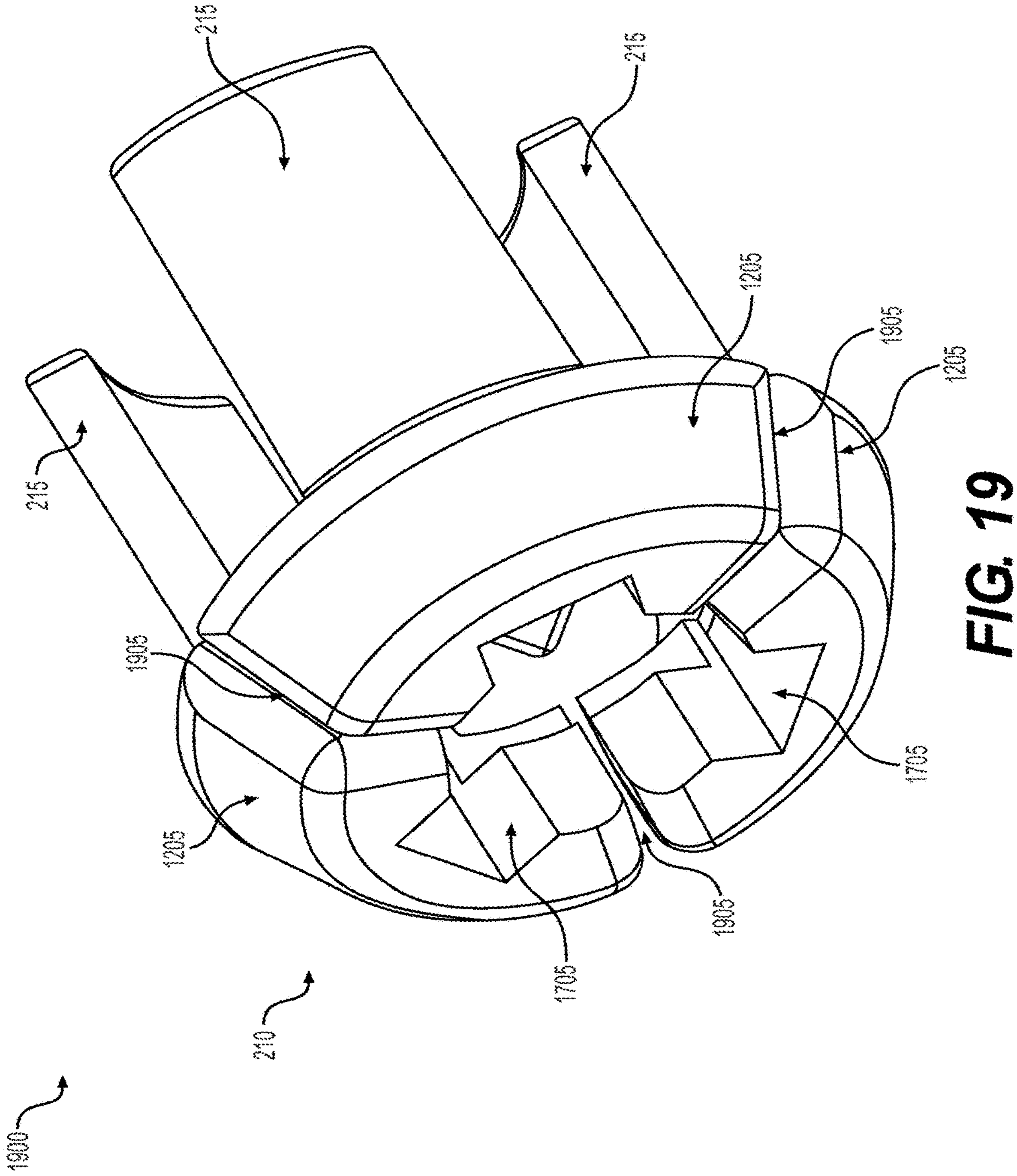
FIG. 19 is a diagram illustrating an isometric bottom view of the exemplary embodiment of the frame structure shown in FIG. 18.

FIG. 19 is a diagram 1900 illustrating an isometric bottom view of the exemplary embodiment of the frame structure shown in FIG. 18. As shown in FIG. 19, the frame segments 1205 have been compressed from the uncompressed configuration shown in FIG. 15 and can interface with one another at one or more segment interfaces 1905.

Figure 20:
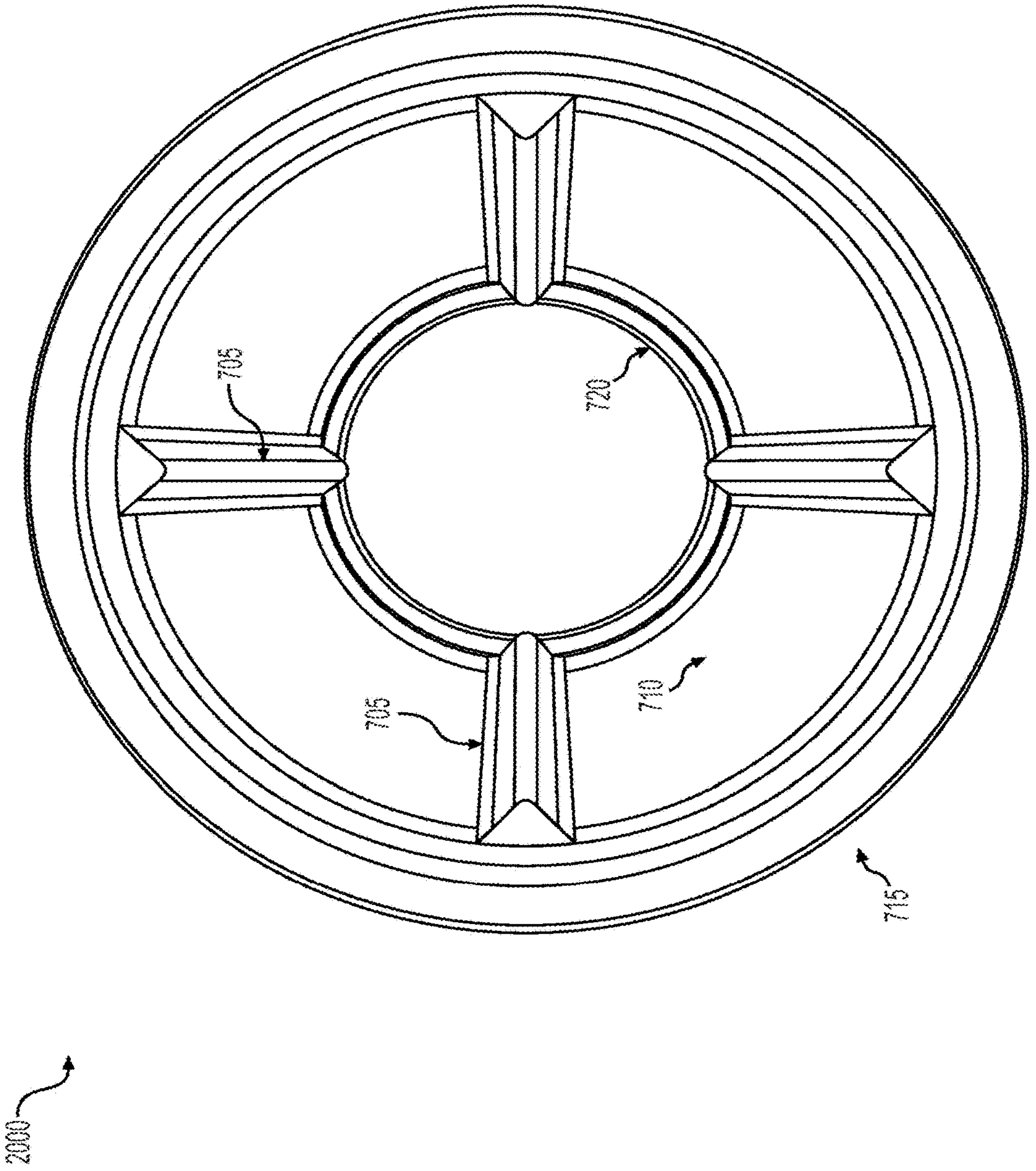
FIG. 20 is a diagram illustrating a perspective cross-sectional view of an exemplary embodiment of a plurality of ribs configured within the shell of the device shown in FIGS. 7 and 8.

FIG. 20 is a diagram 2000 illustrating a perspective cross-sectional view of an exemplary embodiment of a plurality of ribs 705 as shown and described in relation to FIGS. 7 and 8. As shown in FIG. 20, four ribs 705 are formed on the interior surface 710 of the shell 110. The ribs 705 are shown as a non-limiting arrangement in which, the ribs 705 are equally-spaced around the circumference of the interior surface 710. In some embodiments, the ribs 705 may not be equally-spaced around the circumference and can have more ribs 705 or less ribs 705 at one or more circumferential locations of the interior surface 710.

As further shown in FIG. 20, the ribs 705 can include a triangular-shaped cross-section. In some embodiments, the shape of the cross-section of the ribs 705 can be square, rectangular, oval, circular, trapezoidal, or the like, without limitation.

Figure 21:
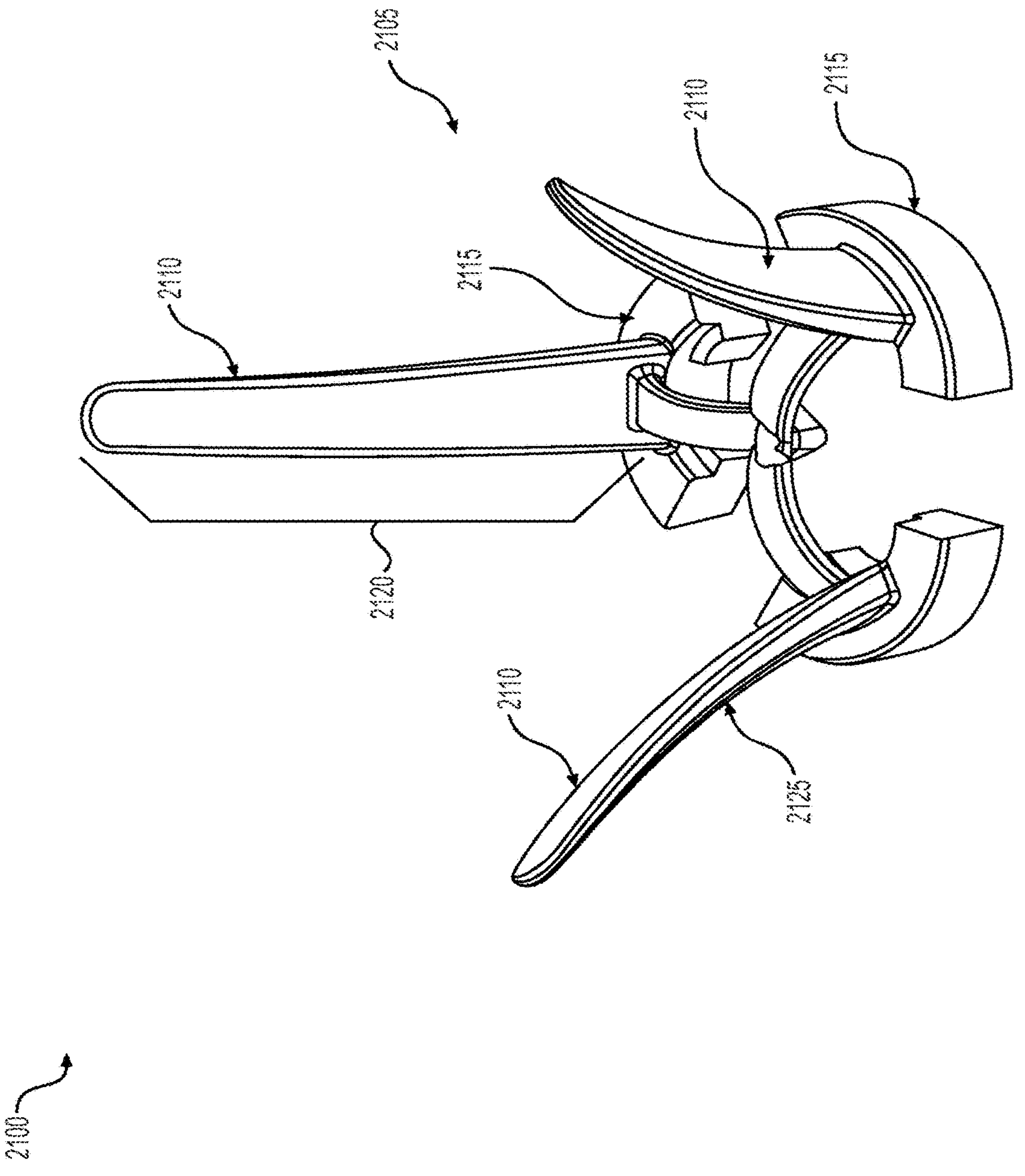
FIG. 21 is a diagram illustrating an isometric top view of another exemplary embodiment of a frame structure of a device for vaginal fluid absorption and odor reduction according to some implementations of the current subject matter.

FIG. 21 is a diagram 2100 illustrating an isometric top view of another exemplary embodiment of a frame structure of a device for vaginal fluid absorption and odor reduction according to some implementations of the current subject matter. The frame structure 2105 shown in FIG. 21 can correspond to the frame structure 210 shown and described in relation to FIGS. 14-19. The frame structure 2105 can include a plurality of frame structure extensions 2110. The frame structure extensions 2110 can each extend from a frame segment 2115. The number of frame structure extensions 2110 and frame segments 2115 can vary. In some embodiments, two or more frame structure extensions 2110 can extend from one frame segment 2115. In some embodiments, a frame segment 2115 may not include a frame structure extension 2110.

As shown in FIG. 21, a frame structure extension 2110 can have a height 2120. The height 2120 can be between 1- and 3.0 cm, although other heights are possible. In some embodiments, the height can be greater than 3.0 cm or less than 1.0 cm. The height 2120 can enable the frame structure extensions 2110 to extend into an absorptive element 205, such as the absorptive elements 205 shown in FIG. 13. In some embodiments, a frame structure extension 2110 can extend into an absorptive element 205 to a distance that is 25-90% of a length of the absorptive element 205.

The frame structure 2110 can include a shape or profile 2125 that can be curved or angled with respect to a corresponding frame segment 2115. The shape or profile 2125 can enable the absorptive elements 205 to more readily open or deploy when the absorptive unit 170 is extended out from the distal end of the device. The actuation of the frame structure 2105 and the frame structure extensions 2110 during deployment can advantageously allow the absorptive unit 170 and the absorptive elements 205 to transition more rapidly and fully to an uncompressed configuration, thereby providing greater absorption of fluids and vaginal odor reduction compared to existing devices.

Exemplary technical effects of the devices and methods described herein include, by way of non-limiting example, absorption of vaginal fluid and reduction in vaginal discomfort and odor. For example, the absorptive elements can expand within the vaginal cavity upon deployment and can conform to the anatomical features of the user's vaginal cavity more effectively. The absorptive elements can include materials, such as polyurethane sponge, which can be configured to increase the absorption of semen from within the vaginal cavity. As a result, vaginal odor and discomfort can be reduced and a more hygienic, healthy environment can be maintained within the vaginal cavity. The absorptive elements can also include contraceptive or spermicidal medicines for reducing the likelihood of pregnancy, as well as other medications for the prevention and/or treatment of diseases, such as sexually transmitted diseases, urinary tract infections, or vaginitis.

Certain exemplary embodiments have been described to provide an overall understanding of the principles of the structure, function, manufacture, and use of the devices, and methods disclosed herein. One or more examples of these embodiments have been illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed devices, and methods, such dimensions are not intended to limit the types of shapes that can be used in conjunction with such devices, and methods. A person skilled in the art will recognize that an equivalent to such linear and circular dimensions can easily be determined for any geometric shape. Sizes and shapes of the devices, and the components thereof, can depend at least on the anatomy of the subject in which the devices will be used, the size and shape of components with which the devices will be used, and the methods and procedures in which the devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, the devices are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

The invention claimed is:

1. A device for absorbing bodily fluids, the device comprising:

a shell;

a plunger defining a proximal end and a distal end, wherein the shell receives the distal end of the plunger, wherein the distal end of the plunger comprises an abutment element and the proximal end of the plunger comprises a flange; and an absorptive unit proximate the distal end of the plunger and configured to absorb fluid within a vaginal cavity, the absorptive unit folded within the shell in a compressed state, wherein the absorptive unit comprises at least two absorptive elements;

a tether structure connected to a base of at least one of the at least two absorptive elements, wherein the abutment element abuts the tether structure when the absorptive unit is in the compressed state, wherein distally advancing the plunger causes the abutment element to push the tether structure to thereby deploy the absorptive unit from the shell, wherein the absorptive unit automatically transitions from a compressed state to an uncompressed state outside of the shell when deployed from the shell.

2. The device of claim 1, wherein at least one of the at least two absorptive elements is petal-shaped.

3. The device of claim 2, wherein at least one of the at least two absorptive elements defines an original size prior to being inserted into the shell and is folded to a compressed size when the absorptive unit is in the compressed state within the shell, wherein the compressed size is less than or equal to 50 percent of the original size.

4. The device of claim 3, wherein, when the absorptive unit is deployed from the shell, the at least one of the at least two absorptive elements unfolds from the compressed size to an uncompressed size when the absorptive unit is in the uncompressed state, wherein the uncompressed size is within a range of 90 to 95 percent of the original size.

5. The device of claim 1, wherein the shell defines an interior surface and an exterior surface, wherein at least a portion of the exterior surface of the shell comprises a gripping area, the gripping area comprising at least one protrusion configured to aid a user in holding the device during insertion of the device into the vaginal cavity.

6. The device of claim 1, wherein, in the uncompressed state, the at least two absorptive elements are fully unfolded.

7. The device of claim 1, wherein at least one of the at least two absorptive elements is configured to contact a vaginal mucosa of the vaginal cavity when the absorptive unit is deployed to thereby absorb the fluid from within the vaginal cavity.

8. The device of claim 1, wherein the absorptive unit is configured to reduce odor within the vaginal cavity.

9. The device of claim 1, wherein the abutment element is disc-shaped.

10. A device for absorbing bodily fluids, the device comprising:

a shell;

a plunger defining a proximal end and a distal end, wherein the shell receives the distal end of the plunger, wherein the distal end of the plunger comprises an abutment element; and an absorptive unit proximate the distal end of the plunger, wherein the shell receives the absorptive unit and the absorptive unit is folded in a compressed state when inside the shell, wherein the absorptive unit comprises at least two absorptive elements;

a tether structure connected to a base of at least one of the at least two absorptive elements, wherein the abutment element abuts the tether structure when the absorptive unit is inside the shell, wherein distally advancing the plunger deploys the absorptive unit from the shell, wherein responsive to deployment of the absorptive unit from the shell, the absorptive unit transitions from the compressed state to an uncompressed state outside of the shell, wherein at least one of the at least two absorptive elements overlaps the other of the at least two absorptive elements when the absorptive unit is folded in the compressed state inside the shell, wherein the absorptive unit is configured to absorb fluid within a vaginal cavity.

11. The device of claim 10, wherein the shell defines a circumference, wherein the at least two absorptive elements at least partially overlaps one another circumferentially with respect to one another when the absorptive unit is received in the shell.

12. The device of claim 11, wherein the at least two absorptive elements at least partially longitudinally overlap when the absorptive unit is received in the shell.

13. The device of claim 10, wherein the plunger comprises a stop and the shell defines a distal end and a proximal end, wherein distally advancing the plunger causes the stop to abut an opening of the proximal end of the shell to cause the absorptive unit to deploy from the shell.

14. The device of claim 13, wherein the shell comprises a gripping area proximate the proximal end of the shell, the gripping area comprising at least one protrusion, wherein the at least one protrusion is a raised circular protrusion extending around a portion of a circumference of the proximal end of the shell and configured to aid a user in holding the device during insertion of the device into the vaginal cavity.

15. The device of claim 10, wherein the abutment element is disc-shaped.

16. The device of claim 10, wherein the absorptive unit is configured to contact the vaginal cavity when expanded to thereby absorb vaginal fluids from within the vaginal cavity.

17. The device of claim 10, wherein, in the uncompressed state, the at least two absorptive elements are fully unfolded.

18. A method of inserting a fluid absorption device into a vaginal cavity, the method comprising:

providing the fluid absorption device in a compressed state, the fluid absorption device comprising:

a shell;

a plunger, wherein the shell receives at least a portion of the plunger, wherein the plunger comprises an abutment element;

an absorptive unit proximate the plunger, wherein the shell receives the absorptive unit, wherein the absorptive unit comprises at least two absorptive elements; and a tether structure connected to a base of at least one of the at least two absorptive elements, wherein the abutment element abuts the tether structure when the absorptive unit is inside the shell;

inserting the fluid absorption device into the vaginal cavity;

advancing the plunger within the shell to deploy the absorptive unit from inside the shell into the vaginal cavity, wherein advancing the plunger within the shell transitions the absorptive unit from the compressed state within the shell to an uncompressed state outside of the shell, wherein at least one of the at least two absorptive elements overlaps the other of the at least two absorptive elements when the absorptive unit is in the compressed state inside the shell; and removing the shell and the plunger from the vaginal cavity.

19. The method of claim 18, further comprising:

removing the absorptive unit from the vaginal cavity after the absorptive unit absorbs a bodily fluid from the vaginal cavity.

20. The method of claim 18, wherein advancing the plunger within the shell causes the abutment element to push the tether structure to thereby deploy the absorptive unit from the compressed state inside the shell to the uncompressed state outside the shell.

* * * * *